United States Patent
White et al.

(10) Patent No.: US 8,563,511 B2
(45) Date of Patent: Oct. 22, 2013

(54) TREATMENT OF PULMONARY HYPERTENSION USING AN AGENT THAT INHIBITS A TISSUE FACTOR PATHWAY

(75) Inventors: R. James White, Rochester, NY (US); Mark B. Taubman, Rochester, NY (US)

(73) Assignee: University of Rochester, Rochester, NY (US)

( * ) Notice: Subject to any disclaimer, the term of this patent is extended or adjusted under 35 U.S.C. 154(b) by 1321 days.

(21) Appl. No.: 11/576,773

(22) PCT Filed: Oct. 6, 2005

(86) PCT No.: PCT/US2005/035990
§ 371 (c)(1),
(2), (4) Date: Oct. 24, 2007

(87) PCT Pub. No.: WO2006/042017
PCT Pub. Date: Apr. 20, 2006

(65) Prior Publication Data
US 2008/0267969 A1    Oct. 30, 2008

Related U.S. Application Data

(60) Provisional application No. 60/616,567, filed on Oct. 6, 2004.

(51) Int. Cl.
*A61K 39/395* (2006.01)

(52) U.S. Cl.
USPC .............. 514/14.5; 424/141.1; 424/143.1; 424/184.1; 514/13.3; 514/15.7; 524/297

(58) Field of Classification Search
None
See application file for complete search history.

(56) References Cited

U.S. PATENT DOCUMENTS

| | | | |
|---|---|---|---|
| 6,017,890 A | 1/2000 | Hoekstra et al. | |
| 6,063,847 A | 5/2000 | Chakalamannil et al. | |
| 6,103,500 A | 8/2000 | Innis et al. | |
| 6,645,987 B2 | 11/2003 | Chakalamannil et al. | |
| 6,946,439 B2 | 9/2005 | Hembrough | |
| 8,299,096 B2 * | 10/2012 | Navratil et al. | 514/322 |
| 8,324,247 B2 * | 12/2012 | Amer | 514/315 |
| 8,410,173 B2 * | 4/2013 | Zisman | 514/619 |
| 2002/0022229 A1 * | 2/2002 | Morse et al. | 435/6 |
| 2002/0102576 A1 * | 8/2002 | Loyd et al. | 435/6 |
| 2003/0039652 A1 * | 2/2003 | Schwarz | 424/146.1 |
| 2003/0199457 A1 | 10/2003 | El-Naggar et al. | |
| 2003/0203927 A1 | 10/2003 | Chakalamannil et al. | |
| 2003/0216437 A1 | 11/2003 | Chakalamannil et al. | |
| 2004/0018516 A1 | 1/2004 | Francischetti et al. | |
| 2004/0033200 A1 * | 2/2004 | Ezban et al. | 424/45 |
| 2004/0152736 A1 | 8/2004 | Chakalamannil et al. | |
| 2004/0192753 A1 | 9/2004 | Chakalamannil et al. | |

FOREIGN PATENT DOCUMENTS

WO    94/03497 A1    2/1994
WO    WO 02087605 A2 *    11/2002

OTHER PUBLICATIONS

Chackalamannil S., "Thrombin receptor antagonists as novel therapeutic targets", Curr Opin Drug Discov Devel. Jul. 2001;4(4):417-27.*
Chakalamannil et al., "Discovery of potent orally active thrombin receptor (protease activated receptor 1) antagonists as novel antithrombotic agents", J Med Chem. Sep. 22, 2005;48(19):5884-7.*
Search Report for European Application 05813918.9, dated Feb. 12, 2010.
Humbert et al., "Treatment of Pulmonary Arterial Hypertension," N. Engl. J. Med. 351(14):1425-1436 (2004).
Collados et al., "Endothelin-1 and Functional Tissue Factor: A Possible Relationship with Severity in Primary Pulmonary Hypertension," Heart Vessels 18:12-17 (2003).
Faul et al., "Triptolide Attenuates Pulmonary Arterial Hypertension and Neointimal Formation in Rates," Am. J. Resp. Critical Care Med. 162:2252-2258 (2000).
Okada et al., "Pulmonary Hemodynamics Modify the Rat Pulmonary Artery Response to Injury," Am. J. Path. 151 (4):1019-1025 (1997).
Zhao et al., Circulation Research 96(4):442-450 (2005).
Derian et al., J. Pharmacol. Exp. Ther. 304(2):855-861 (2003).
Ahn et al., Biochem. Pharmacol. 60(10):1425-1434 (2000) (abstract only).
Bernatowicz et al., J. Med. Chem. 39:4879-4887 (1996) (abstract only).
Barrow et al., Bioorg. Med. Chem. Lett. 11:2691-2696 (2001) (abstract only).
Zhang et al., Bioorg. Med. Chem. Lett. 13:2199-2203 (2003) (abstract only).
Nantermet et al., Bioorg. Med. Chem. Lett. 12:319-23 (2002) (abstract only).

* cited by examiner

*Primary Examiner* — Michael Szperka
(74) *Attorney, Agent, or Firm* — LeClairRyan, a Professional Corporation

(57) ABSTRACT

An improved non-human animal model of severe pulmonary arterial hypertension (PAH) and its use for testing of therapeutic agents that can treat symptoms of PAH are disclosed. In addition, the present application relates to the identification of several classes of therapeutic agents that, alone or in combination, can be used to treat or prevent PAH or at least reduce the severity of symptoms associated therewith. Both gene therapy and non-gene therapy approaches are described.

19 Claims, 6 Drawing Sheets

```
SEQUENCE LISTING

<160> NUMBER OF SEQ ID NOS: 2

<210> SEQ ID NO 1
<211> LENGTH: 9
<212> TYPE: PRT
<213> ORGANISM: Artificial
<220> FEATURE:
<223> OTHER INFORMATION: PAR-1 antagonist
<220> FEATURE:
<221> NAME/KEY: MISC_FEATURE
<222> LOCATION: (1)..(1)
<223> OTHER INFORMATION: Xaa at position 1 is 3-mercaptoproprionyl-
      phenylalanine
<220> FEATURE:
<221> NAME/KEY: MISC_FEATURE
<222> LOCATION: (2)..(3)
<223> OTHER INFORMATION: Xaa at position 2 and 3 is 3-cyclohexylalanine
<220> FEATURE:
<221> NAME/KEY: MISC_FEATURE
<222> LOCATION: (9)..(9)
<223> OTHER INFORMATION: Xaa at position 9 is amidated lysine

<400> SEQUENCE: 1

Xaa Xaa Xaa Arg Lys Pro Asn Asp Xaa
1               5

<210> SEQ ID NO 2
<211> LENGTH: 5
<212> TYPE: PRT
<213> ORGANISM: Artificial
<220> FEATURE:
<223> OTHER INFORMATION: PAR-4 antagonist
<220> FEATURE:
<221> NAME/KEY: MISC_FEATURE
<222> LOCATION: (1)..(1)
<223> OTHER INFORMATION: Xaa at position 1 is trans-cinnamoyl-tyrosine
<220> FEATURE:
<221> NAME/KEY: MISC_FEATURE
<222> LOCATION: (5)..(5)
<223> OTHER INFORMATION: Xaa at position 5 is amidated phenylalanine

<400> SEQUENCE: 2

Xaa Pro Gly Lys Xaa
1               5
```

TREATMENT OF PULMONARY HYPERTENSION USING AN AGENT THAT INHIBITS A TISSUE FACTOR PATHWAY

This application is a national application under 35 U.S.C. 371 of PCT/US05/035990 filed Oct. 6, 2005, and claims the priority benefit of U.S. Provisional Patent Application Ser. No. 60/616,567, filed Oct. 6, 2004, which is hereby incorporated by reference in its entirety.

This invention was made with government support under grant number HL054469 awarded by NIH. The government has certain rights in the invention.

FIELD OF THE INVENTION

The present invention relates to an animal model of pulmonary arterial hypertension ("PAH") that more closely approximates the condition as manifested in humans, use of the model to identify or screen therapeutic agents that can treat or prevent PAH, and methods of treating or preventing PAH (or symptoms thereof) using tissue factor ("TF") inhibitors or inhibitors of TF-mediated pathways.

BACKGROUND OF THE INVENTION

Severe PAH is the marked elevation of precapillary resistance in the pulmonary circulation which occurs sporadically and in families as an idiopathic form. It is also observed in association with diseases such as chronic venous thromboembolism, scleroderma, HIV infection, and cirrhosis (Fishman, "Etiology and Pathogenesis of Primary Pulmonary Hypertension: A Perspective," *Chest* 114(3 Suppl):242S-247S (1998); Farber et al., "Pulmonary Arterial Hypertension," *New Engl. J. Med.* 351(16):1655-65 (2004)). PAH is a rare but devastating disease mainly affecting young women, although the increased incidence of PAH among patients with scleroderma and cirrhosis is changing the demographics of the illness. Survival is dismal with untreated advanced patients having a 50% six-month mortality.

The widespread introduction of continuous prostacyclin infusion in 1996 revolutionized treatment for the disease (Barst et al., "A Comparison of Continuous Intravenous Epoprostenol (Prostacyclin) with Conventional Therapy for Primary Pulmonary Hypertension. The Primary Pulmonary Hypertension Study Group," *New Engl. J. Med.* 334(5):296-302 (1996)) and has markedly improved survival—60% three year survival with contemporary therapy (Kawut et al., "New Predictors of Outcome in Idiopathic Pulmonary Arterial Hypertension," *Am. J. Cardiol.* 95(2):199-203 (2005)).

Unfortunately, there are still only five drugs with regulatory approval for the treatment of this unusual illness (Farber et al., "Pulmonary Arterial Hypertension," *New Engl. J. Med.* 351(16):1655-65 (2004); Humbert et al., "Treatment of Pulmonary Arterial Hypertension," *New Engl. J. Med.* 351(14): 1425-36 (2004)), and many patients progress to lung transplantation or death despite the best available therapy. Even considering the progress made in treating patients, an understanding of the disease process remains limited (Newman et al., "Pulmonary Arterial Hypertension: Future Directions: Report of a National Heart, Lung and Blood Institute/Office of Rare Diseases Workshop," *Circulation* 109(24):2947-52 (2004)).

In advanced PAH of many etiologies, endothelial proliferation and medial hypertrophy ultimately obliterate the arterial lumen. Most patients also have disordered angiogenesis in glomeruloid-like structures called plexiform lesions (Pietra et al., "Histopathology of Primary Pulmonary Hypertension. A Qualitative and Quantitative Study of Pulmonary Blood Vessels from 58 Patients in the National Heart, Lung, and Blood Institute, Primary Pulmonary Hypertension Registry," *Circulation* 80(5):1198-206 (1989); Meyrick, "The Pathology of Pulmonary Artery Hypertension," *Clin. Chest Med.* 22(3):393-404 (2001); Tuder et al., "Exuberant Endothelial Cell Growth and Elements of Inflammation are Present in Plexiform Lesions of Pulmonary Hypertension," *Am. J. Pathol.* 144(2):275-85 (1994)). Plexiform lesions are not seen in any disease of the systemic arterial circulation. However, these unique structures do share a resemblance with the vessels in a rare form of cancer, glioblastoma multiforme (Tuder et al., "Exuberant Endothelial Cell Growth and Elements of Inflammation are Present in Plexiform Lesions of Pulmonary Hypertension," *Am J Pathol* 144(2):275-85 (1994)), and the cells that make up the lesions may be causative in the progression of PAH. There is some data from human autopsy studies to support the hypothesis that plexiform lesions precede the development of concentric luminal obliteration and are therefore critical to the vascular remodeling (Cool et al., "Three-Dimensional Reconstruction of Pulmonary Arteries in Plexiform Pulmonary Hypertension Using Cell-Specific Markers. Evidence for a Dynamic and Heterogeneous Process of Pulmonary Endothelial Cell Growth," *Am. J. Pathol.* 155(2):411-9 (1999)). Thus, proliferative vascular lesions and concentric luminal obliteration would be desirable in an animal model of severe PAH to study the mechanisms that mediate this unusual proliferation of vascular endothelial and smooth muscle cells (Newman et al., "Pulmonary Arterial Hypertension: Future Directions: Report of a National Heart, Lung and Blood Institute/Office of Rare Diseases Workshop," *Circulation* 109(24):2947-52 (2004); Tuder et al., Exuberant Endothelial Cell Growth and Elements of Inflammation are Present in Plexiform Lesions of Pulmonary Hypertension," *Am. J. Pathol.* 144(2):275-85 (1994); Humbert et al., "Cellular and Molecular Pathobiology of Pulmonary Arterial Hypertension," *J. Amer. Coll. Cardiol.* 43(12 Suppl S):13S-24S (2004); Rubin et al., "Pulmonary Arterial Hypertension: a Look to the Future," *J. Amer. Coll. Cardiol.* 43(12 Suppl S):89S-90S (2004)). Such a model would also be very useful for rational drug development.

The endothelial toxin monocrotaline ("MCT") is commonly used to produce an experimental model of PAH in which the animals develop a "rugged" appearing endothelium and medial hypertrophy. However, two pathologic hallmarks of human disease, concentric luminal obliteration and plexiform lesions, are not observed. In the rat model pioneered by Botney, MCT is administered to rats following left pneumonectomy. These animals develop more severe PAH with neointimal formation and concentric obliteration in most of the distal pulmonary vessels (Okada et al., "Pulmonary Hemodynamics Modify the Rat Pulmonary Artery Response to Injury. A Neointimal Model of Pulmonary Hypertension," *Am. J. Pathol.* 151(4):1019-25 (1997)), much like that seen in human disease. While these models have been useful in defining important pathways of vascular remodeling and thus suggesting novel treatment strategies (Cowan et al., "Elastase and Matrix Metalloproteinase Inhibitors Induce Regression, and Tenascin-C Antisense Prevents Progression, of Vascular Disease," *J. Clin. Invest.* 105(1):21-34 (2000); Nishimura et al., "Simvastatin Rescues Rats from Fatal Pulmonary Hypertension by Inducing Apoptosis of Neointimal Smooth Muscle Cells," *Circulation* 108(13):1640-5 (2003); Zhao et al., "Rescue of Monocrotaline-Induced Pulmonary Arterial Hypertension Using Bone Marrow-Derived Endothelial-Like Progenitor Cells: Efficacy of Combined Cell and eNOS Gene Therapy in Established Disease," *Circ. Res.* 96(4):442-450

(2005)), the absence of some classic pathologic features of human disease is an important limitation for both models. Plexiform lesions have not been reported in these rats or any other animal model of PAH.

It would be desirable, therefore, to develop an animal model of severe PAH that can more accurately reflect the symptoms exhibited by human patients, including both luminal obliteration and formation of plexiform (or plexiform-like) lesions. Such a model, if developed, would be more likely to provide reliable observations for the testing or screening of therapeutic agents that can be used to treat or prevent PAH (or manage symptoms thereof).

The present invention is directed to overcoming these and other deficiencies in the art.

SUMMARY OF THE INVENTION

A first aspect of the present invention relates to a method of inhibiting the loss of small blood vessel beds associated with an arterial trunk in lung tissue that includes: providing a therapeutic agent that inhibits tissue factor activity or a tissue factor-mediated downstream signaling pathway; and contacting vascular cells in a small blood vessel bed associated with an arterial trunk in lung tissue with the therapeutic agent, wherein said contacting inhibits vascular cell loss in the small blood vessel bed.

A second aspect of the present invention relates to a method of preventing or treating neointimal formation in lung vascular tissue that includes: providing a therapeutic agent that inhibits tissue factor activity or a tissue factor-mediated downstream signaling pathway; and contacting (i) vascular cells prior to neointimal or plexiform lesion development or (ii) a neointimal or plexiform lesion formation in lung vascular tissue, with the therapeutic agent, wherein said contacting inhibits development of a neointimal or plexiform lesion formation or reduces the size of the existing neointimal or plexiform lesion in lung vascular tissue.

A third aspect of the present invention relates to a method of treating pulmonary hypertension that includes: providing a therapeutic agent that inhibits tissue factor activity or a tissue factor-mediated downstream signaling pathway; and administering the therapeutic agent to a patient symptomatic with pulmonary hypertension, wherein said administering is effective to reduce the extent of plexiform lesions or to reduce the extent of neointimal obliteration of small vessels in lung vascular tissue, thereby enhancing vascular capacity and treating pulmonary hypertension.

A fourth aspect of the present invention relates to a method of inhibiting the loss of small blood vessel beds associated with an arterial trunk in lung tissue that includes: providing (i) a genetic construct encoding a polypeptide that inhibits tissue factor activity or a tissue factor-mediated downstream signaling pathway or (ii) a transgenic cell that expresses the polypeptide; and either introducing the genetic construct into vascular cells in a small blood vessel bed associated with an arterial trunk in lung tissue or introducing the transgenic cell into a small blood vessel bed associated with an arterial trunk in lung tissue, wherein said introducing inhibits vascular cell loss in the small blood vessel bed.

A fifth aspect of the present invention relates to a method of preventing or treating neointimal or plexiform lesion formation in lung vascular tissue that includes: providing a genetic construct encoding a polypeptide that inhibits tissue factor activity or a tissue factor-mediated downstream signaling pathway or (ii) a transgenic cell that expresses the polypeptide; and either (i) introducing the genetic construct or transgenic cell into lung vascular tissue prior to neointimal or plexiform lesion development or (ii) introducing the genetic construct or transgenic cell into a neointimal or plexiform lesion formation, wherein said introducing inhibits progression of neointimal or plexiform lesion formation or reduces the size of existing neointimal or plexiform lesion in lung vascular tissue.

A sixth aspect of the present invention relates to a method of treating pulmonary hypertension that includes: providing a genetic construct encoding a polypeptide that inhibits tissue factor activity or a tissue factor-mediated downstream signaling pathway; and either introducing the genetic construct or introducing the transgenic cell into small vessels in lung vascular tissue of a patient symptomatic with pulmonary hypertension, wherein said introducing is effective to reduce the extent of plexiform lesions or to reduce the extent of neointimal obliteration of small vessels in lung vascular tissue, thereby enhancing vascular capacity and treating pulmonary hypertension.

A seventh aspect of the present invention relates to a non-human animal model of pulmonary arterial hypertension. The animal model is a juvenile animal that is treated with pneumonectomy followed by administration of monocrotaline, wherein the treated juvenile animal in the absence of intervention develops symptoms of pulmonary arterial hypertension that include formation of plexiform-like lesions. According to a preferred embodiment, the animal model is a rodent model.

An eighth aspect of the present invention relates to a method of screening a therapeutic agent for use in treating pulmonary arterial hypertension that includes administering a therapeutic agent to an animal model according to the seventh aspect of the invention, and determining whether said administering alters development of symptoms of pulmonary arterial hypertension.

To understand better the relationship between plexiform lesions and disease progression, a rat model was developed to better replicate the form of PAH observed in humans. Specifically, the rat model displayed proliferative vascular lesions and obliteration of the pulmonary arterial lumen. These rats developed plexiform-like lesions and the hemodynamic alterations typical of human disease. The animals appeared to be more severely affected because they died faster than rats in previous reports (Okada et al., "Pulmonary Hemodynamics Modify the Rat Pulmonary Artery Response to Injury. A Neointimal Model of Pulmonary Hypertension," *Am. J. Pathol.* 151(4):1019-25 (1997); Faul et al., "Triptolide Attenuates Pulmonary Arterial Hypertension and Neointimal Formation in Rats," *Am. J. Respir. Crit. Care Med.* 162(6): 2252-8 (2000), each of which is hereby incorporated by reference in its entirety). Some of the plexiform lesions expressed endothelial antigens similar to those of human disease, and they appeared to be connected to the pulmonary artery. TF antigen was markedly increased in the vessels and proliferative lesions of these rats. In addition, there was a marked increase in TF antigen levels in plexiform lesions and in vessels with medial hypertrophy in the lungs of humans with PAH. This supports the demonstrated use of TF pathway inhibitors for treating or preventing PAH.

BRIEF DESCRIPTION OF TILE DRAWINGS

FIG. 1 is a graph that illustrates the effects of monocrotaline treatment following pneumonectomy on the development of severe pulmonary arterial hypertension on animals (as compared with sham operated animals given monocrotaline). Following anesthesia, rats were ventilated through a tracheostomy and the chest was opened. The right ventricular wall was punctured with a fluid-filled catheter and pressure measurements were made before advancing the catheter into the pulmonary artery. As expected, rats treated with sham operation+vehicle (n=6) had normal pulmonary pressures. Surprisingly, pneumonectomy+vehicle animals also had normal pulmonary hemodynamics (n=6). MCT treatment following sham surgery resulted in modest PAH as reported by others (n=8), and the rats given MCT after pneumonectomy (n=3) had near systemic elevations in pulmonary pressure ($p<0.03$, ANOVA followed by multiple comparisons with Bonferonni). Data are shown as mean±SEM; RVSP, right ventricular systolic pressure; mean PA, mean pulmonary artery pressure.

FIGS. 2A-E illustrate the histological effects of MCT treatment following pneumonectomy, specifically the neointimal changes and development of plexiform-like lesions heavily stained with tissue factor. Rat lung tissue was immunostained with a polyclonal antibody to tissue factor. All photomicrographs were taken at 20×. The developer is NovoRed, so all pink or red staining is the result of tissue factor antigen. FIG. 2A is an image of an arteriole from a rat treated with vehicle (DMSO) injection following pneumonectomy, which shows faint TF reactivity in a histologically normal vessel. The vessels shown in FIGS. 2B-E are from rats treated with MCT following pneumonectomy. FIG. 2B shows a small hypertrophied arteriole with an endothelium, and media that is heavily stained with TF. FIG. 2C shows a pair of vessels nearly obliterated with intimal hyperplasia and medial hypertrophy. TF staining is present throughout the vessel wall. FIGS. 2D-E illustrate proliferative, plexiform like lesions from two different animals.

FIGS. 3A-D illustrate the histological analyses of plexiform-like lesions in rat models of severe pulmonary arterial hypertension. The lesions have vascular channels and cells stain for both mature and immature endothelial cell markers. FIG. 3A is a 10× micrograph illustrating a plexifonn-like lesion adjacent to an obliterated arteriole. The lungs had been perfused with fluorescein microparticles at sacrifice, and the particles confirm communicating vascular channels in this lesion (FIG. 3B, 40×, arrows). Serial sections were immunostained with antibodies to von Willebrand's Factor ("vWF") (FIG. 3C) and Vascular Endothelial Growth Factor Receptor-2 ("VEGF-R2") (FIG. 3D). As in FIGS. 2 & 4, Novo-Red was used as the developer, so all pink and red staining is therefore attributable to the antigen. The two different endothelial cell markers indicate that vWF (+) cells line channels (FIG. 3C) while the VEGF-R2 antibody stains a diffuse population of immature endothelial and inflammatory cells (FIG. 3D). The appearance of the channels at different places in the serial sections confirms the impression of disorganized vascular channels.

FIGS. 4A-E illustrate the expression levels of tissue factor antigen in plexifonn lesions of human patients with pulmonary arterial hypertension. Photomicrographs (all 20× magnification) of human lung immunostained with a polyclonal antibody against TF were then developed with Novo-Red; all pink and red staining is therefore attributable to TF antigen. FIG. 4A shows a pulmonary arteriole from normal lung with faint endothelial staining and a quiet media. TF-positive cells can be found in the adjacent epithelium and TF-positive monocytes can be found in the alveolar spaces. FIG. 4B illustrates TF staining in the media and endothelium of a vessel with relatively early disease (medial hypertrophy). FIG. 4C shows moderate staining in the center of a concentric, onion-skin lesion while FIGS. 4D-E illustrate intense and diffuse staining in two different plexiform lesions. Bronchial epithelium expresses TF normally and is shown as a positive control (Epi) (FIG. 4D). The micrographs in FIGS. 4B-E are from four different patients listed in Table 1 (see Examples infra).

DETAILED DESCRIPTION OF THE INVENTION

Figure 1:
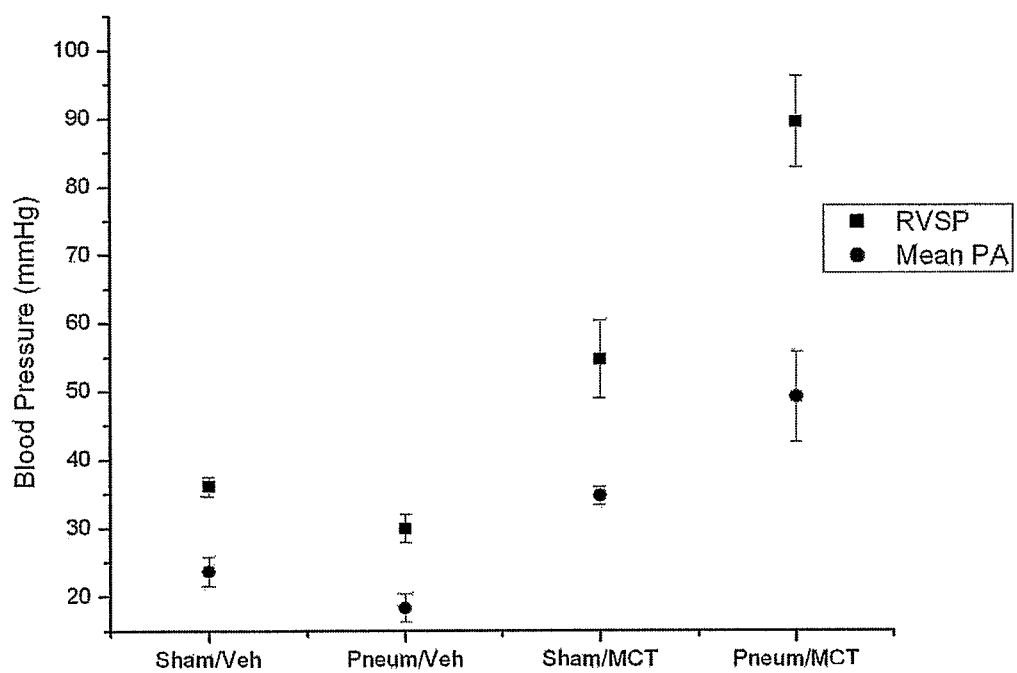

The present invention relates to an improved model of severe pulmonary arterial hypertension (PAH) and its use for testing of therapeutic agents that can treat symptoms of PAH. In addition, the present application relates to the identification of several classes of therapeutic agents that, alone or in combination, can be used to treat or prevent PAH or at least reduce the severity of symptoms associated therewith.

One aspect of the present invention relates to a non-human animal model of severe pulmonary arterial hypertension. The model is obtained using a juvenile animal that is treated with pneumonectomy followed by administration of monocrotaline ("MCT"). In the absence of intervention, the treated juvenile animal will develop signs and symptoms of pulmonary arterial hypertension that include, without limitation, elevated pulmonary blood pressure (i.e., relative to control), formation of plexiform-like lesions, neointimal formation with obliteration of the vasculature, right ventricular hypertrophy, exercise intolerance, and earlier mortality (i.e., relative to control untreated with MCT).

The monocrotaline is preferably administered about 5 to about 9 days post-pneumonectomy, more preferably about 6 to about 8 days post-pneumonectomy, most preferably 7 days post-pneumonectomy.

The non-human animal can be any mammal, including without limitation a rodent, cat, dog, pig, or non-human primate. The mammal is preferably a juvenile animal. According to a preferred embodiment, the non-human animal is a juvenile rat that is less than about 300 g, preferably between about 200 to about 250 g.

The animal model thus obtained is suitable for use in screening therapeutic agents as potential treatments for pulmonary arterial hypertension in other animals, including humans. Screening of therapeutic agents can be performed by administering a therapeutic agent to an animal model according to the present invention, and then determining whether administration of the therapeutic agent alters development of signs or symptoms of pulmonary arterial hypertension. Basically, the therapeutic agent can be administered any time subsequent to monocrotaline administration. In one approach, the therapeutic agent can be administered soon after MCT administration (i.e., from about 2 hours to about 7 days, preferably from about 1 to about 5 days) to assess the ability of the therapeutic agent to halt or reverse early signs or symptoms of PAH. In another approach, the therapeutic agent can be administered well after MCT administration (i.e., from about 7 to about 14 days, preferably from about 9 to about 12 days) to assess the ability of the therapeutic agent to halt or reverse advanced signs or symptoms of PAH.

Administration of the therapeutic agent can be carried out orally, by inhalation, by intranasal instillation, topically, transdermally, parenterally, subcutaneously, by intravenous injection, intra-arterial injection, intramuscular injection, intrapleural instillation, intraperitoneal injection, intraventricular injection, intralesional injection, or by application to mucous membranes. Administration can be repeated, i.e., up to two-to-five times daily either indefinitely or for a duration that is suitable to achieve a desired endpoint such as relief of symptoms or a defined period in which symptoms normally arise. Alternatively, administration of the therapeutic agent can also be continuous for a duration that is suitable to achieve a desired endpoint.

Assessment of the efficacy of a therapeutic agent can be determined by comparing the results achieved with the therapeutic agent against a known standard (i.e., mean blood pressure in control animals with PAH or exemplary histological specimen representative of control animals with PAH) or against control animals raised under otherwise identical conditions (i.e., in a direct comparison to samples and measurements obtained from a side-by-side control animal).

As demonstrated in the Examples (infra), applicants have identified tissue factor (TF) as a causative agent in the onset of PAH in the above model. TF is a transmembrane glycoprotein that initiates the coagulation cascade and may also facilitate angiogenesis, both in development and in tumor growth (Mackman, "Regulation of the Tissue Factor Gene," *Thromb. Haemost.* 78(1):747-54 (1997); Bachli, "History of Tissue Factor," *Brit. J. Haematol.* 110(2):248-55 (2000); Riewald et al., "Orchestration of Coagulation Protease Signaling by Tissue Factor," *Trends Cardiovasc. Med.* 12(4):149-54 (2002), each of which is hereby incorporated by reference in its entirety). TF expression is markedly upregulated in the arterial wall following experimental arterial injury (Hatakeyama et al., "Expression of Tissue Factor in the Rabbit Aorta After Balloon Injury," *Atherosclerosis* 139(2):265-71 (1998), which is hereby incorporated by reference in its entirety), and its inhibition has been shown to attenuate intimal hyperplasia in a variety of animal models (reviewed in Taubman et al., "Regulation of the Procoagulant Response to Arterial Injury," *Thromb Haemost* 82(2):801-5 (1999), which is hereby incorporated by reference in its entirety). Since PAH is a disease with a thrombotic diathesis (Pietra et al., "Histopathology of Primary Pulmonary Hypertension. A Qualitative and Quantitative Study of Pulmonary Blood Vessels from 58 Patients in the National Heart, Lung, and Blood Institute, Primary Pulmonary Hypertension Registry," *Circulation* 80(5):1198-206 (1989); Fuster et al., Primary Pulmonary Hypertension: Natural History and the Importance of Thrombosis," *Circulation* 70(4):580-7 (1984), each of which is hereby incorporated by reference in its entirety), given the results demonstrated herein TF likely plays a key role in disease progression.

Consequently, inhibition of TF activity or inhibition of a TF-mediated downstream signaling pathway (i.e., one that is activated directly or indirectly by TF) can be used to treat or prevent signs or symptoms of PAH, including pathological conditions associated therewith. As used herein, inhibition of TF activity is intended to encompass inhibition of TF enzymatic activity (that normally results in Factor Xa generation), inhibition of intracellular signaling activity within the cytoplasmic domain, or both. In particular, inhibition of TF or TF-mediated downstream signaling pathways can be used to inhibit pathological conditions selected from the group of small blood vessel bed loss in lung tissue, and neointimal and/or plexiform-like lesion formation in lung vascular tissue; and to reduce the severity of or ameliorate symptoms of PAH including high pulmonary blood pressure and exercise intolerance.

Exemplary therapeutic agents that inhibit TF activity include, without limitation, tissue factor pathway inhibitor (TFPI) such as recombinant TFPI (Tifacogin™ available from Chiron Corp.), a TFPI mimetic such as Ixolaris (available from Dr. Ivo Francischetti of the NIAID), anti-TF monoclonal or polyclonal antibodies, site-inactivated Factor VIIa (Novo Nordisk), and anti-Factor VII monoclonal or polyclonal antibodies.

Exemplary therapeutic agents that inhibit TF-mediated downstream signaling pathways include, without limitation, anti-Factor Xa antibody (Cuo Pharmaceuticals), direct acting thrombin inhibitors such as hiruidin (Refludan™, Berlex) and ximelagatran (Exanta™, Astra Zeneca), and protease-activated receptor ("PAR") blockers, which include small molecule, peptide, and monoclonal or polyclonal antibody antagonists of PAR-1, PAR-2, and PAR-4.

Suitable PAR-1 antagonists include, without limitation, SCH205831 (also known as (3R,3aS,4S,4aR,8aS,9aR,E)-3-methyl-4-(2-(5-(3-(trifluoromethyl)phenyl)pyridin-2-yl)vinyl)-decahydronaphtho[2,3-c]furan-1(3H)-one) (Chackalamannil et al., "Discovery of Potent Orally Active Thrombin Receptor (Protease Active Receptor 1) Antagonists as Novel Antithrombotic Agents," *J. Med. Chem.* 48(19):5884-5887 (2005), which is hereby incorporated by reference in its entirety); FR171113 (also known as 2-[3-(4-Chlorophenyl)-2-[(2,4-dichlorobenzoyl)imino]-4-oxo-5-thiazolidinylidene]-acetic acid methyl ester) (Kato et al., "Inhibition of Arterial Thrombosis by a Protease-Activated Receptor 1 Antagonist, FR171113, in the Guinea Pig," *Eur. J. Pharmacol.* 473(2-3):163-167 (2003), which is hereby incorporated by reference in its entirety); RWJ58259 (also known as (αS)—N-[(1S)-3-amino-1-[[(phenylmethyl)-amino]carbonyl]propyl]-α-[[[[[1-(2,6-dichlorophenyl)methyl]-3-(1-pyrrolidinylmethyl)-1H-indazol-6-yl]amino]carbonyl]amino]-3,4-difluorobenzenepropanamide) (Andrade-Gordon et al., "Administration of a Potent Antagonist of Protease-Activated Receptor-1 (PAR-1) Attenuates Vascular Restenosis Following Balloon Angioplasty in Rats,"*J. Pharmacol Exp. Ther.* 298(1):34-42 (2001); Derian et al., "Blockade of Thrombin Receptor Protease-Activated Receptor-1 with a Small Molecule Antagonist Prevents Thrombus Formation and Vascular Occlusion in Nonhuman Primates," *J. Pharmacol. Exp. Ther.* 304(2):855-861 (2003) (erratum 305(1):402 (2003), each of which is hereby incorporated by reference in its entirety)); SCH79797 (also known as N3-cyclopropyl-7-[[4-(1-methylethyl)phenyl]methyl]-7H-pyrrolo[3,2-f]quinazoline-1,3-diamine) and SCH203099 (also known as N3-cyclopropyl-7-(4-isopropylbenzyl)-N1-methyl-7H-pyrrolo[3,2-f] quinazoline-1,3-diamine) (Ahn et al., "Inhibition of Cellular Action of Thrombin by N3-cyclopropyl-7-[[4-(1-methylethyl)phenyl]methyl]-7H-pyrrolo[3,2-f]quinazoline-1,3-diamine (SCH 79797), a Nonpeptide Thrombin Receptor Antagonist," *Biochem. Pharmacol.* 60(10):1425-1434 (2000), which is hereby incorporated by reference in its entirety); and peptide derivative 3-mercaptoproprionyl-Phe-Cha-Cha-Arg-Lys-Pro-Asn-Asp-Lys-$NH_2$ (Sigma-Aldrich, Inc.). Monoclonal and polyclonal antibodies would also be suitable PAR-1 blockers.

Suitable PAR-2 antagonists include, without limitation, peptide p520 and the small molecule 547m, both available Entremed, Inc., and anti-PAR-2 antibodies.

Suitable PAR-4 antagonists include, without limitation, YD-3 (Wu et al., "Selective Inhibition of Protease-Activated Receptor 4-dependent Platelet Activation by YD-3," *Thrombosis Haemostasis* 87:1026-1033 (2002), which is hereby incorporated by reference in its entirety); and trans-cinnamoyl-Tyr-Pro-Gly-Lys-Phe-$NH_2$ (SEQ ID NO: 2, Quinton et al., "Plasmin-mediated Activation of Platelets Occurs by Cleavage of Protease-activated Receptor 4," *J. Biol. Chem.* 279(18)18434-18439 (2004), which is hereby incorporated by reference in its entirety).

According to one embodiment, the loss of small blood vessel beds (associated with an arterial trunk in lung tissue) can be inhibited. In this embodiment, vascular cells in a small blood vessel bed are contacted with the therapeutic agent and such contacting is effective to inhibit vascular cell loss in the small blood vessel bed. Vascular cells can include both endothelial cells and vascular smooth muscle cells.

According to another embodiment, neointimal and/or plexiform lesion formation in lung vascular tissue can be prevented (i.e., prior to onset) or treated (i.e., after onset). In this embodiment, vascular cells in lung vascular tissue are contacted prior to neointimal and/or plexiform lesion development or, alternatively, a neointimal and/or plexiform lesion in lung vascular tissue is contacted, with the therapeutic agent, wherein said contacting inhibits progression of a neointimal and/or plexiform lesion formation or reduces the size of the existing neointimal and/or plexiform lesion in lung vascular tissue.

According to a further embodiment, PAH can be treated by administering the therapeutic agent to a patient that is symptomatic for PAH. The administration of the therapeutic agent is effective to reduce signs or symptoms of PAH, including, without limitation, the proliferative, plexiform lesions or the extent of neointimal obliteration of small vessels in lung vascular tissue, thereby enhancing vascular capacity and treating pulmonary hypertension.

In the above embodiments, contacting of vascular cells includes endothelial cells, vascular smooth muscle cells, or inflammatory cells (i.e., recruited to the cite of neointimal formations) that are in vivo within a mammal. Administration to a patient is contemplated. These can be accomplished either via systemic administration to the patient or via targeted administration to the vascular cells of lung vascular tissue. Exemplary routes of administration include, without limitation, orally, by inhalation, by intranasal instillation, topically, transdermally, parenterally, subcutaneously, intravenous injection, intra-arterial injection (such as via the pulmonary artery), intramuscular injection, intrapleural instillation, intraperitoneal injection, intraventricular injection, intralesional injection, or by application to mucous membranes. Of these, intravenous, intra-arterial (pulmonary), intraventricular, and inhalation routes of administration are preferred.

The mammal to be treated in accordance with the present invention can be a rodent, dog, cat, cow, horse, sheep, pig, llama, alpaca, non-human primate, or human.

The administration of the therapeutic agent can be carried out as frequently as required and for a duration that is suitable to provide effective treatment for PAH or its underlying pathological conditions. For example, administration of the therapeutic agent can be carried out with a single sustained-release dosage formulation or with multiple daily doses of the therapeutic agent. The amount to be administered will, of course, vary depending upon the treatment regimen.

Typically, the therapeutic agent will be administered to a mammal as a pharmaceutical composition that includes the therapeutic agent and any pharmaceutically acceptable suitable adjuvants, carriers, excipients, or stabilizers, and can be in solid or liquid form such as, tablets, capsules, powders, solutions, suspensions, or emulsions. The compositions preferably contain from about 0.01 to 99 weight percent, more preferably from about 2 to 60 percent, of therapeutic agent together with the adjuvants, carriers and/or excipients. The amount of active compound in such therapeutically useful compositions is such that a suitable dosage unit will be obtained. Preferred compositions according to the present invention are prepared so that a single dosage unit contains between about 1 mg and 1000 mg of the therapeutic agent.

In addition to the administration of therapeutic agents, various gene therapy approaches are contemplated for treating PAH and its associated signs or symptoms as described above. In the various gene therapy approaches, a genetic construct is utilized for transformation of cells, preferably patient cells, either in vivo or ex vivo. In the latter case the cells are collected from the patient to be treated, transformed, and then reintroduced into the patient.

Gene therapy approaches for treating these conditions utilize an expression vector or plasmid that contains therein a recombinant gene (or genetic construct) encoding a therapeutic protein or nucleic acid. Exemplary therapeutic proteins encoded by the recombinant gene include, without limitation, tissue factor pathway inhibitor (TFPI, Genbank Accessions NM_006287 (TFPI var. 1), NM_001032281 (TFPI, var. 2), and NM_006528 (TFPI2), each of which is hereby incorporated by reference in its entirety), tissue factor pathway inhibitor mimetics such as Ixolaris (IXO, Genbank Accession AF286029, which is hereby incorporated by reference in its entirety) and Ixolaris-2 (IXO-2, Genbank Accession AY674279, which is hereby incorporated by reference in its entirety), and peptide inhibitors of PARs such as those described above.

The recombinant gene includes, operatively coupled to one another, an upstream promoter operable in mammalian cells and optionally other suitable regulatory elements (i.e., enhancer or inducer elements), a coding sequence that encodes the therapeutic protein or nucleic acid (described above), and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in endothelial cells, such as the Tie2 promoter (Minami et al., "Ets Motifs are Necessary for Endothelial Cell-specific Expression of a 723-bp Tie-2 Promoter/Enhancer in hprt targeted transgenic mice," *Arterioscl. Thromb. Vasc. Biol.* 23(11):2041-2047 (2003), which is hereby incorporated by reference in its entirety), or in vascular smooth muscle cells, such as SM22 (Ribault et al., "Chimeric Smooth Muscle-Specific Enhancer/Promoters: Valuable Tools for Adenovirus-mediated Cardiovascular Gene Therapy," *Circulation Res.* 88(5):468-475 (2001), which is hereby incorporated by reference in its entirety). Tissue specific promoters can also be made inducible/repressible using, e.g., a TetO response element. Known recombinant techniques can be utilized to prepare the recombinant gene, transfer it into the expression vector, and administer the vector to a patient. Exemplary procedures are described in Sambrook et al., *Molecular Cloning: A Laboratory Manual*, Second Edition, Cold Spring Harbor Press, N.Y. (1989), which is hereby incorporated by reference in its entirety. One of skill in the art can readily modify these procedures, as desired, using known variations of the procedures described therein.

The recombinant gene can be delivered into targeted cells (to be transformed) as either naked DNA that can be taken up by the cell, or by using a viral (infective) vector or a non-infective delivery vehicle.

Any suitable viral or infective transformation vector can be used. Exemplary viral vectors include, without limitation, adenovirus, adeno-associated virus, retroviral vectors, Adenovirus gene delivery vehicles can be readily prepared and utilized given the disclosure provided in Berkner, *Biotechniques* 6:616-627 (1988) and Rosenfeld et al., *Science* 252:431-434 (1991), WO 93/07283, WO 93/06223, and WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired protein or polypeptide or nucleic acid. The use of adeno-associated viral gene delivery vehicles in vitro is described in Chatterjee et al., *Science* 258:1485-1488 (1992); Walsh et al., *Proc. Nat'l Acad. Sci. USA* 89:7257-7261 (1992); Walsh et al., *J. Clin. Invest.* 94:1440-1448 (1994); Flotte et al., *J. Biol. Chem.* 268:3781-3790 (1993); Ponnazhagan et al., *J. Exp. Med.* 179:733-738 (1994); Miller et al., *Proc. Nat'l Acad. Sci. USA* 91:10183-10187 (1994); Einerhand et al., *Gene Ther.* 2:336-343 (1995); Luo et al., *Exp. Hematol.* 23:1261-1267 (1995); and Zhou et al., *Gene Ther.* 3:223-229 (1996), each of which is hereby incorporated by reference in its entirety. In vivo use of these vehicles is described in Flotte et al., *Proc. Nat'l Acad. Sci. USA* 90:10613-10617 (1993); and Kaplitt et al., *Nature Genet.* 8:148-153 (1994), each of which is hereby incorporated by reference in its entirety.

Retroviral vectors which have been modified to form infective transformation systems can also be used to deliver a recombinant gene encoding a desired protein or polypeptide or nucleic acid product into a target cell. One such type of retroviral vector is disclosed in U.S. Pat. No. 5,849,586 to Kriegler et al., which is hereby incorporated by reference in its entirety.

Alternatively, a number of non-infective delivery vehicles are available for delivering the genetic construct in vivo or ex vivo. A colloidal dispersion system can be used to deliver the genetic construct to a patient. Colloidal dispersion systems include macromolecule complexes, nanocapsules, microspheres, beads, and lipid-based systems including oil-in-water emulsions, micelles, mixed micelles, and liposomes. The preferred colloidal system of this invention is a lipid preparation including uni-lamellar and multi-lamellar liposomes.

Liposomes are artificial membrane vesicles that are useful as delivery vehicles in vitro and in vivo. It has been shown that large uni-lamellar vesicles (LUV), which range in size from about 0.2 to about 4.0 µm, can encapsulate a substantial percentage of an aqueous buffer containing DNA molecules (Fraley et al., *Trends Biochem. Sci.* 6:77 (1981), which is hereby incorporated by reference in its entirety). In addition to mammalian cells, liposomes have been used for delivery of polynucleotides in yeast and bacterial cells. For a liposome to be an efficient transfer vehicle, the following characteristics should be present: (1) encapsulation of the DNA molecules at high efficiency while not compromising their biological activity; (2) substantial binding to host organism cells; (3) delivery of the aqueous contents of the vesicle to the cell cytoplasm at high efficiency; and (4) accurate and effective expression of genetic information (Mannino et al., *Biotechniques* 6:682 (1988), which is hereby incorporated by reference in its entirety). In addition to such LUV structures, multilamellar and small unilamellar lipid preparations which incorporate various cationic lipid amphiphiles can also be mixed with anionic DNA molecules to form liposomes (Felgner et al., *Proc. Natl. Acad. Sci. USA* 84(21): 7413 (1987), which is hereby incorporated by reference in its entirety).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and typically the presence of divalent cations. The appropriate composition and preparation of cationic lipid amphiphile:DNA formulations are known to those skilled in the art, and a number of references which provide this information are available (e.g., Bennett et al., *J. Liposome Research* 6(3):545 (1996), which is hereby incorporated by reference in its entirety).

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. Examples of cationic amphiphilic lipids useful in formulation of nucleolipid particles for polynucleotide delivery include the monovalent lipids N-[1-(2,3-dioleoyloxy)propyl]-N,N,N,-trimethyl ammonium methyl-sulfate, N-[2,3-dioleoyloxy)propyl]-N,N,N-trimethyl ammonium chloride, and DC-cholesterol, the polyvalent lipids LipofectAMINE™, dioctadecylamidoglycyl spermine, Transfectam®, and other amphiphilic polyamines. These agents may be prepared with helper lipids such as dioleoyl phosphatidyl ethanolamine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization. The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

A further alternative for delivery of DNA is the use of a polymeric matrix which can provide either rapid or sustained release of the genetic construct to the organism. A number of polymeric matrices are known in the art and can be optimized with no more than routine skill.

The genetic constructs can be used either for direct administration to a patient, in which patient cell transformation occurs in vivo, or for ex vivo transformation of previously harvested patient cells that can then be reintroduced into the patient to be treated.

Preferred routes for administering a genetic construct for in vivo transformation include (i) administering the genetic construct (as either an infective vector or as a component within a delivery vehicle) into the right ventricle or a peripheral vein of the patient, and (ii) administering the genetic construct (as a component of a delivery vehicle) via inhalation. Either of these routes will effectively cause the genetic construct to be delivered into small arterial vessels of lung tissue.

When using ex vivo transformation, it is preferable to harvest progenitor stem cells from the patient, including progenitor endothelial cells or progenitor vascular smooth muscle cells. After harvesting (and optionally purifying the population of cells), the harvested progenitor cells are transformed, transformants are selected, and then the transformed progenitor cells are reintroduced into the lung tissue of the patient. Reintroduction of the transformed cells is preferably carried out by right ventricular administration or peripheral intravenous administration. The ex vivo transformation of endothelial progenitor cells is described in Zhao et al., "Rescue of Monocrotaline-Induced Pulmonary Arterial Hypertension Using Bone Marrow-Derived Endothelial-Like Progenitor Cells: Efficacy of Combined Cell and eNOS Gene Therapy in Established Disease," *Circ. Res.* 96(4):442-450 (2005), which is hereby incorporated by reference in its entirety).

According to one embodiment, the loss of small blood vessel beds (associated with an arterial trunk in lung tissue) can be inhibited by providing either (i) a genetic construct encoding an inhibitor of TF activity or a TF-mediated downstream signaling pathway or (ii) a transgenic cell that expresses an inhibitor of TF activity or a TF-mediated downstream signaling pathway. The genetic construct can be introduced (in vivo) into vascular cells in a small blood vessel bed associated with an arterial trunk in lung tissue. Alternatively, the ex vivo transgenic vascular cell can be introduced into a small blood vessel bed associated with an arterial trunk in lung tissue. In either case, the presence of the transformed vascular cell in the small blood vessel beds results in expression of the therapeutic agent and thereby inhibits vascular cell (endothelial, vascular, or both) loss in the small blood vessel bed According to another embodiment, neointimal or plexiform formation in lung vascular tissue can be prevented (i.e., prior to onset) or treated (i.e., after onset) by providing either (i) a genetic construct encoding an inhibitor of TF activity or a TF-mediated downstream signaling pathway or (ii) a transgenic cell that expresses an inhibitor of TF activity or a TF-mediated downstream signaling pathway. The genetic construct or the transgenic vascular cell can be introduced into lung vascular tissue either prior to neointimal or plexiform lesion development or into a neointimal or plexiform lesion. In either case, presence of the transformed cell in lung vascular tissue results in expression of the therapeutic agent, and thereby inhibits progression of the neointimal or plexiform lesion formation or reduces the size of the existing neointimal or plexiform lesion in lung vascular tissue.

According to a further embodiment, PAH can be treated using a genetic construct encoding either (i) a genetic construct encoding an inhibitor of TF activity or a TF-mediated downstream signaling pathway or (ii) a transgenic cell that expresses an inhibitor of TF activity or a TF-mediated downstream signaling pathway. The genetic construct or the transgenic cell can be introduced into small vessels in lung vascular tissue. In either case, presence of transformed cells in lung vascular tissue results in expression of the therapeutic agent, and thereby reduces the extent of plexiform lesions or reduces the extent of neointimal obliteration of small vessels in lung vascular tissue, or both. This effectively enhanced vascular capacity, and thereby treats the pulmonary hypertension.

EXAMPLES

The following examples are provided to illustrate embodiments of the present invention but are by no means intended to limit its scope.

Materials and Methods

Human Subjects:

Tissue already obtained from University of Colorado PAH patients undergoing lung transplant (n=5) or autopsy examination (n=5) was utilized, and informed consent to use the tissue for research purposes had been obtained. Unused donor lungs without evidence for pulmonary vascular disease (n=6) served as controls. The characteristics of patients from whom tissue samples were obtained are provided in Table 1 below.

TABLE 1

Patient Characteristics

| Patient | Age | Disease State | Anticoagulation |
|---------|-----|---------------|-----------------|
| A-99-30 | 40 | IPAH[a] | Yes |
| C-451-91 | n/a | APAH[b] | n/a |
| A-97-164 | 48 | IPAH | Yes |
| A-95-157 | 30 | APAH | Yes |
| A-99-15 | 30 | APAH | Yes |
| S-97-8972 | 37 | APAH | Yes |
| S-99-9004 | n/a | IPAH | Yes |
| S-02-3170 | 23 | IPAH | Yes |
| S-02-4504 | 28 | IPAH | Yes |
| S-02-14559 | 55 | IPAH | Yes |
| NL 9 | 22 | CVA[c] | No |
| NL 10 | 17 | CVA | No |
| NL 11 | 71 | CVA | No |
| NL 13 | 75 | CVA | No |
| NL 14 | 69 | CVA | n/a |
| NL 24 | 74 | CVA | No |

[a]IPAH, idiopathic pulmonary arterial hypertension (formerly PAH);
[b]associated pulmonary arterial hypertension;
[c]CVA, cerebrovascular accident Histopathology:

Paraffin embedded human lung tissue from the University of Colorado was sectioned at 5 μm on a microtome. The TF immunohistochemistry in humans and rats employed a polyclonal anti-human TF antibody raised in rabbits against the extracellular domain (residues 1-218) of TF (soluble TF, sTF) which had been expressed in *Escherichia coli* (Marmur et al., "Identification of Active Tissue Factor in Human Coronary Atheroma," *Circulation* 94(6):1226-32 (1996), which is hereby incorporated by reference in its entirety).

The rat tissues were fixed in 10% neutral formalin, processed and embedded in paraffin. Sections were cut at 5 μm, deparaffinized and rehydrated through graded alcohols. After quenching in 3% hydrogen peroxide, slides were antigen retrieved using a pressure cooker in 10 mM Citrate Buffer at pH 6. The slides were blocked in the appropriate serum (Vector Laboratories, Burlingame, Calif.) and the primary antibody applied overnight at 4° C. Immunodetection was performed by using biotinylated secondaries (Vector Laboratories, Burlingame, Calif.), peroxidase-labeled streptavidin (Jackson Immuno Research, West Grove, Pa.), and Nova Red as the developer (Vector Laboratories, Burlingame, Calif.). The slides were then counterstained in hematoxylin. An appropriate positive control was used for each stain, and the primary antibody was omitted for the negative control.

Animals:

All animal studies were approved by the IACUC at the University of Rochester prior to the initiation of any animal experiments. Male Sprague Dawley rats weighing between 200 and 250 g were shaved and then endotracheally intubated with an 18 G angiocatheter after anesthesia with ketamine and xylazine (70 mg/kg ketamine and 50 mg/kg xylazine delivered intraperitoneal in 0.9% saline). Flunixin was administered 0.1 mg/kg SQ at the beginning of the case to provide 24 hours postoperative analgesia. Animals were ventilated (respiratory rate 70-90, adjusted while monitoring the animal to prevent spontaneous respiratory effort) at 10-12 cc/kg (Harvard Apparatus) and the left chest was prepared with Betadine scrub. The fourth or fifth intercostal space was identified, and an incision was made with care to avoid lung damage while ventilation was briefly interrupted. A rib retractor was used to expose the thoracic cavity, and the lung was lifted gently to expose the hilar structures. Two ligaclips (Ektacon LS200, Johnson & Johnson) were applied proximally before the left lung was cut at the distal hilar structure. A polyethylene tube with holes at the end and cut into the sides was inserted through the sixth intercostal space and laid in the thoracic cavity where the left lung had been. Two absorbable sutures were used to approximate the ribs, and then the muscles and subcutaneous tissue were approximated with an additional layer of sutures. Care was taken to carefully seal the thoracostomy tube with tissue so that the hole would close spontaneously when the thoracostomy tube was removed. Suction was applied to the tubing at the earliest possible time once a seal had been achieved (sometimes before the subcutaneous tissues were closed). Antisedan (Orion) was administered 0.2 mg/kg IM, and the skin was closed with 9 mm Autoclips (Stoelting). The animal was taken off the ventilator and monitored for spontaneous respirations while suction was applied to the thoracostomy tube. The rat was required to make significant respiratory effort and begin to right itself on the table before the endotracheal and thoracostomy tubes were removed. Animals were observed for three to four hours on a heating pad before being placed in their cages. A 30 to 40% mortality is routinely encountered in the 24 hour perioperative period. For the sham surgery, an incision was made to the chest wall. With great care, ventilation was stopped, the chest was listed with forceps, and a small incision was made in the fourth or fifth intercostal space. If there was any evidence for lung damage, the case was converted to a pneumonectomy. A smaller polyethylene tube was inserted through the same hole and laid between the lung and the chest wall. The ribs were approximated with one or two sutures as appropriate. The remainder of the procedure was identical. The animal was ventilated for several minutes after the chest was closed but before sedation was reversed to make sure that total time under anesthesia was approximately the same as in pneumonectomy cases.

One week later, animals were given MCT (dissolved 60 mg/ml in DMSO) as a subcutaneous injection (vehicle animals were treated with the same volume of DMSO alone). They were monitored and allowed ordinary chow and water for 28 days (in the group of animals which were utilized to generate FIG. 2, two of the animals initially treated with pneumonectomy and MCT died spontaneously on days 18 and 23, so the remaining four animals were sacrificed at Day 24).

Exercise capacity was monitored 5 and 10 days after MCT treatment and then more frequently as the disease progressed. Rats were placed on a treadmill (Columbus Instruments) that stimulates them with a mild electric shock when they fail to run. Each assessment lasted for 16 min: 2 min. @ 10 m/min, 4 min @ 15 m/min, 5 min @ 20 m/min, and 5 min @ 25 m/min. The maximum distance run was 305 m. This procedure has been specifically approved by the local IACUC.

Prior to surgery, rats had an initial orientation and then two formal training sessions; this helped minimize inter-animal variability at baseline. Initially, a grid intensity of 70% maximum and frequency of 2 Hz was used. Animals were conditioned to avoid the stimulus grid, and at this stage, they were stimulated for 10 sec before the grid was turned off. A brush was used to encourage the animals to continue running when they fell behind on the treadmill or if they sat on the stimulus grid. 10 days after MCT or Veh injection, the protocol for stimulation changed. By this time, some rats developed clinically significant disease. In addition, the rats had five exposures to the treadmill and were sufficiently averse to the stimulus grid that the intensity of the stimulus was no longer be as important in determining their aversion. Because the goal is a submaximal exertion (specifically not exhaustion), the animals were encouraged to choose stimulation over exercise when they were tired. Animals received the ordinary stimulation for the first 3 min. At 3 min, the stimulus grid was turned down to 25% of its maximal intensity and rats were stimulated for 5 sec before the grid was turned off. At 7 min, rats only needed to be stimulated for 3 sec before the grid was turned off.

At the time of sacrifice, rats were anesthetized with ketamine and xylazine (80 mg/kg ketamine & 30 mg/kg xylazine intraperitoneally). The entire abdomen, chest, and neck were shaved. A percutaneous tracheostomy was quickly performed and the animals were ventilated in the supine position. Mid-axillary incisions through the rib cage were made and the entire anterior rib cage was lifted up as a single unit with care to avoid damage to the lung parenchyma. A single 6-0 silk suture was carefully placed through the left ventricle to provide some tension on the heart, and a 21 G needle was used to pierce the right ventricular wall close to the right ventricular outflow tract. A fluid-filled catheter was quickly inserted into the same hole and pressure measurements were made with a Power Lab apparatus connected to a Macintosh computer. Analog signals were digitized at 100 Hz, and 10-60 seconds of reproducible cardiac cycles were recorded. The catheter was then advanced into the main pulmonary artery before more measurements were taken.

The left atrium was cut and the lungs were perfused with phosphate buffered saline through the main pulmonary artery. In some animals, 0.2 micron fluorescein microspheres (Molecular Probes, Eugene, Oreg.) were suspended in 1% low melting point agarose and injected following the saline flush as previously described (Zhao et al., "Rescue of Monocrotaline-Induced Pulmonary Arterial Hypertension Using Bone Marrow-Derived Endothelial-Like Progenitor Cells: Efficacy of Combined Cell and eNOS Gene Therapy in Established Disease," *Circ. Res.* 96(4):442-450 (2005), which is hereby incorporated by reference in its entirety). The lungs were then inflation fixed with 4% paraformaldehyde using a 20 cm column to provide uniform inflation. The heart was removed and the chambers were weighed. After 48-72 hours of paraformaldehyde, the lungs were transferred to 70% ethanol. After an additional 24 hours, the right lower lobe tissue was cut into blocks and paraffin embedded.

VEGF-R2 (flk-1) antibody was purchased from Santa Cruz and vWF antibody from Dako.

Figure 2:
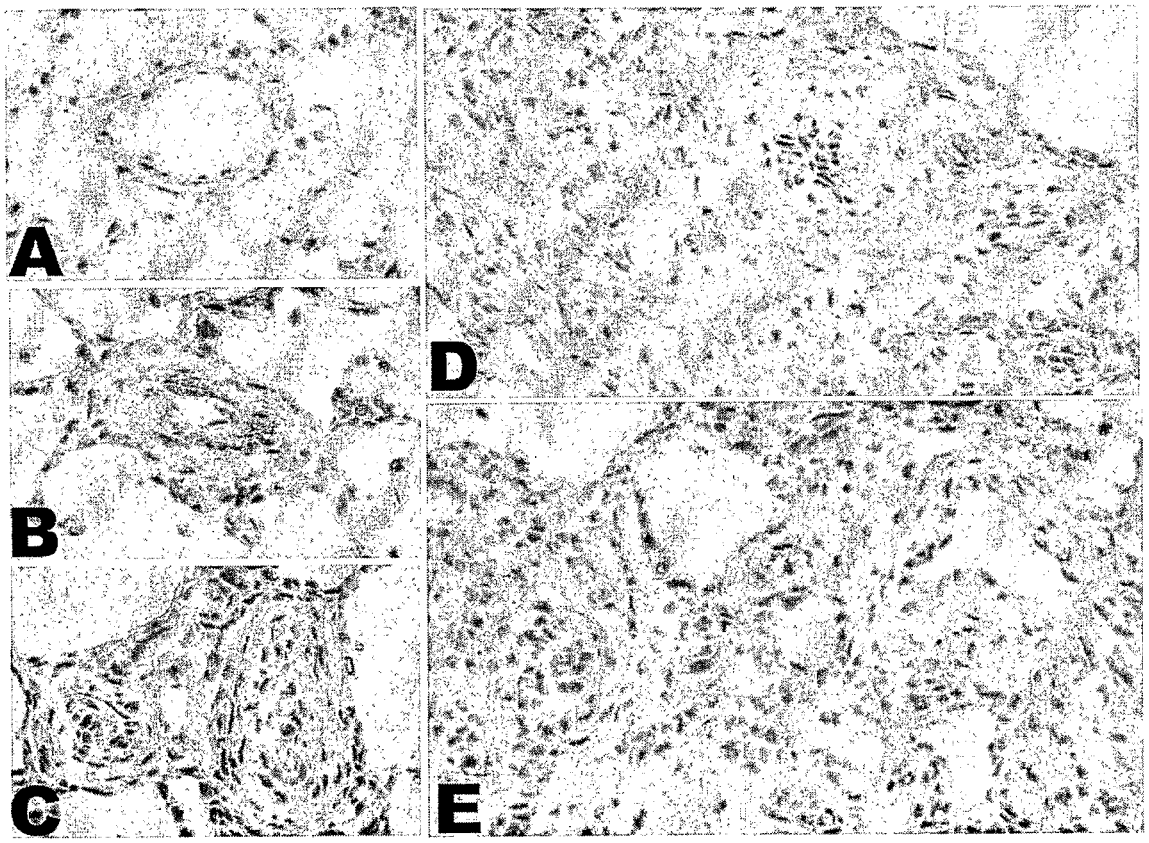

Statistical Analysis:

Hemodynamic data was analyzed with the Mac Lab software to generate the summary data shown in FIG. 2. Representative tracings (at least 4 cardiac cycles) were highlighted; the computer software then generated unbiased means and peak pressures. The four groups (sham+vehicle, sham+MCT, pneumonectomy+vehicle, pneumonectomy+MCT) were first compared using an analysis of variance with an alpha level of 0.05. If the groups differed, between group comparisons were made with a Bonferroni correction for multiple comparisons (Unistat Light, London, England). The same statistical analysis was performed for the heart weight data shown in Table 2 below.

TABLE 2

Severe Right Ventricular Hypertrophy Was Observed After MCT Administration to Pneumonectomized Rats

| Treatment | (RV + S)/ LV | (RV + S)/ Weight | LV/ Weight |
| --- | --- | --- | --- |
| Sham/Vehicle | 0.6 ± 0.0 | 1.2 ± 0.1 | 1.9 ± 0.1 |
| Pneumo/Vehicle | 0.6 ± 0.1 | 1.2 ± 0.2 | 2.0 ± 0.2 |
| Sham/MCT | 1.20 ± 0.3 ** | 1.9 ± 0.4 | 1.6 ± 0.2 |
| Pneumo/MCT | 1.8 ± 0.6 ** | 2.7 ± 0.3 | 1.6 ± 0.5 |

Because the septum becomes a functional part of the right ventricle (RV) in severe PAH, RV hypertrophy was calculated as the weight of the (RV+septum)/left ventricular weight. RV hypertrophy occurred in animals that received monocrotaline following a sham procedure, but the degree of right ventricular hypertrophy was much greater in those that received monocrotaline after a pneumonectomy (** $p<0.03$, one way ANOVA followed by post hoc testing between the two groups with a Bonferroni correction).

Example 1

Severe PAH and Plexiform Like Lesions Develop after MCT Administration to Pneumonectomized Rats Young rats (200 g, about 6 weeks old) were subjected to a left pneumonectomy or sham surgery. One week later, they were given a single dose of MCT (60 mg/kg, SQ) or vehicle injection. The initial reports using older rats showed data from animal sacrificed 28 days following MCT administration (Okada et al., "Pulmonary Hemodynamics Modify the Rat Pulmonary Artery Response to Injury. A Neointimal Model of Pulmonary Hypertension," Am. J. Pathol. 151(4): 1019-25 (1997); Faul et al., "Triptolide Attenuates Pulmonary Arterial Hypertension and Neointimal Formation in Rats," Am. J. Respir. Crit. Care Med. 162(6):2252-8 (2000), each of which is hereby incorporated by reference in its entirety). 28 day experiments were planned, but due to two spontaneous deaths prior to Day 24 in the pneumonectomy+MCT group, the remaining rats treated with pneumonectomy+MCT were sacrificed earlier than initially planned at Day 24. FIG. 1 shows that these rats (n=3) had more severe elevations in their mean PA pressure as compared with rats treated with MCT following a sham surgery (n=8; p<0.03). Interestingly, pneumonectomy+vehicle had no effect on mean PA pressure (n=6) compared with sham-operated, vehicle treated animals (n=6). Because the septum becomes a functional part of the right ventricle (RV) in severe PAH, RV hypertrophy was calculated as the weight of the (RV+septum)/left ventricular weight. Table 2 demonstrates that RV hypertrophy accompanied the increase in mean PA pressure. RV hypertrophy was increased in animals treated with pneumonectomy+MCT as compared to sham+MCT (p<0.03).

Exercise capacity was assessed three times prior to MCT or vehicle injection on "Day 0," and then regularly throughout the remaining 17 days. Performance on the test was very consistent once trained. Rats with Pneum/MCT began to lose exercise capacity 10 days after MCT, and by day 17 nearly all Pneum/MCT rats were unable to complete the 16 min protocol. In contrast, rats in the Pneum/Veh and the Sham/MCT groups consistently completed the exercise protocol. The experiment was terminated after 17 days because of inability to exercise and early deaths in the Pneum/MCT group. These data suggest that the treadmill test is sensitive to the development of PAH and provides a non-invasive tool to follow the efficacy of interventions designed to attenuate PAH.

Figure 3:
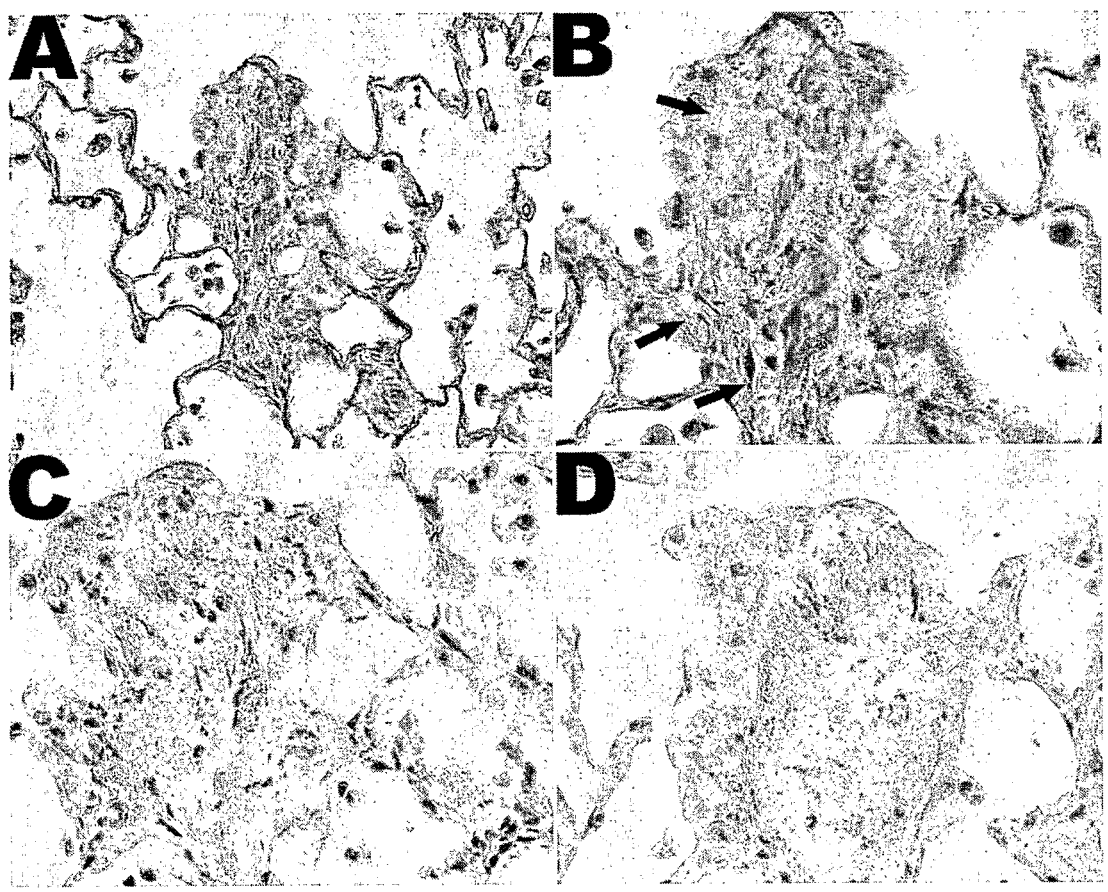
Figure 4:
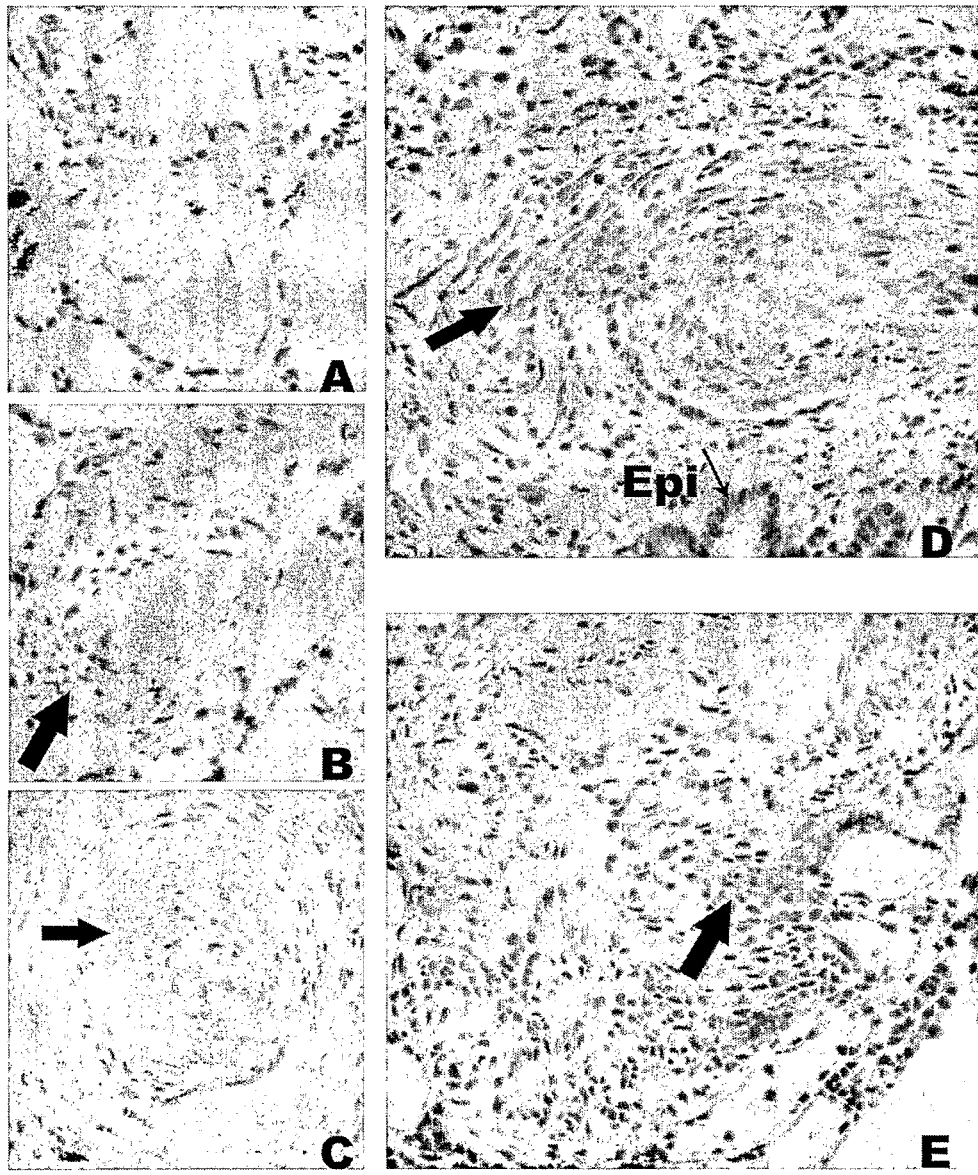

The alveolar epithelium was relatively well preserved in MCT-injured animals following sham surgery or pneumonectomy (see FIG. 2A & FIG. 3A). Both groups displayed severe medial hypertrophy (FIG. 2B). As previously reported (Okada et al., "Pulmonary Hemodynamics Modify the Rat Pulmonary Artery Response to Injury. A Neointimal Model of Pulmonary Hypertension," Am. J. Pathol. 151(4):1019-25 (1997); Faul et al., "Triptolide Attenuates Pulmonary Arterial Hypertension and Neointimal Formation in Rats," Am. J. Respir. Crit. Care Med. 162(6):2252-8 (2000), each of which is hereby incorporated by reference in its entirety), smaller arterioles were frequently obliterated in the animals treated with pneumonectomy and MCT (FIG. 2C). This was not seen in sham+MCT animals. A distinctive finding in this study was the high frequency of perivascular, proliferative lesions (see FIG. 2D, 2E, and FIG. 3), which appeared remarkably similar to those from human patients with PAH (compare FIGS. 2D & 2E with FIGS. 4D & 4E). These lesions are therefore referred to as "plexiform-like."

To determine the origin of these plexiform-like lesions, the main PA was flushed at the time of euthanasia with a solution containing fluorescein microparticles (Zhao et al., "Rescue of Monocrotaline-Induced Pulmonary Arterial Hypertension Using Bone Marrow-Derived Endothelial-Like Progenitor Cells: Efficacy of Combined Cell and eNOS Gene Therapy in Established Disease," Circ. Res. 96(4):442-450 (2005); Han et al., "Defective Lung Vascular Development and Fatal Respiratory Distress in Endothelial NO Synthase-Deficient Mice: a Model of Alveolar Capillary Dysplasia?" Circ. Res. 94(8):1115-23 (2004), each of which is hereby incorporated by reference in its entirety). As shown in FIG. 3, these microparticles are seen as small yellow grains within the spaces of the plexiform-like lesion. This suggests that these lesions contain vascular structures that communicate with the main pulmonary artery. Plexiform-like lesions from humans stain with markers for both endothelial cells (von Willebrand's Factor, vWF) and vascular smooth muscle (smooth muscle alpha-actin, SMA) (Cool et al., "Three-Dimensional Reconstruction of Pulmonary Arteries in Plexiform Pulmonary Hypertension Using Cell-Specific Markers. Evidence for a Dynamic and Heterogeneous Process of Pulmonary Endothelial Cell Growth," Am. J. Pathol. 155(2):411-9 (1999), which is hereby incorporated by reference in its entirety). To better characterize the cellular phenotypes in the plexiform-like lesions from rats, immunostaining was performed in serial sections with antibodies to vascular endothelial growth factor receptor-2 (VEGF-R2) and vWF. The rat plexiform-like lesion contained vWF expressing cells (FIG. 3C) lining vascular channels whereas immature endothelial cells staining for VEGF-R2 were more uniformly distributed (FIG. 3D). This pattern of staining is similar to that reported for human plexiform lesions (Cool et al., "Three-Dimensional Reconstruction of Pulmonary Arteries in Plexiform Pulmonary Hypertension Using Cell-Specific Markers. Evidence for a Dynamic and Heterogeneous Process of Pulmonary Endothelial Cell Growth," Am. J. Pathol. 155(2):411-9 (1999), which is hereby incorporated by reference in its entirety). Therefore, this model recapitulates many of the pathologic features seen in human idiopathic PAH.

Example 2

Tissue Factor is Induced in the Vessels and Plexiform-Like Lesions of Rats Treated with Pneumonectomy & MCT Tissue factor (TF) is a transmembrane glycoprotein that initiates the coagulation cascade and may also facilitate angiogenesis, both in development and in tumor growth (Mackman, "Regulation of the Tissue Factor Gene," *Thromb. Haemost.* 78(1):747-54 (1997); Bachli, "History of Tissue Factor," *Brit. J. Haematol.* 110(2):248-55 (2000); Riewald et al., Orchestration of Coagulation Protease Signaling by Tissue Factor," *Trends Cardiovasc. Med.* 12(4):149-54 (2002), each of which is hereby incorporated by reference in its entirety). Since PAH is a disease in which a thrombotic diathesis is recognized, lung tissue was stained with a polyclonal antibody raised against the soluble portion of TF protein. Rats undergoing pneumonectomy followed by vehicle treatment had normal PA pressures (FIG. 1) and very little medial TF staining (FIG. 2A). In contrast, young rats subjected to MCT following pneumonectomy demonstrated marked TF staining in the wall of vessels that were hypertrophied (FIG. 2B) and in those that were nearly obliterated (FIG. 2C). TF staining was intense in vascular cells throughout the plexiform-like lesions (FIGS. 2D & 2E).

Example 3

Tissue Factor Antigen is Markedly Increased in the Plexiform Lesions of Patients with PAH To confirm the relevance of finding TF association with plexiform-like lesions, presence of TF in human disease was assessed using lung tissue obtained from PAH patients who were undergoing transplant (n=5) or at autopsy (n=5). Normal human tissue was obtained when lungs were not used for transplant because of technical reasons not having to do with the tissue itself (n=6). The patients were followed at the University of Colorado Pulmonary Hypertension Center; the relevant clinical data is in Table 1 above. The group includes patients with idiopathic disease and those whose PAH was associated with scleroderma, anorexigens, or HIV. Tissue factor (TF) was almost never seen in the media of vessels in normal patients although faint endothelial staining was occasionally noted (FIG. 1A); in contrast, patients with PAH had prominent medial TF staining even in vessels with relatively early abnormalities (FIG. 1B). TF staining was heavy in vessels that were obliterated by typical concentric proliferation (FIG. 1C) and was particularly intense in most plexiform lesions (FIGS. 1D & 1E). Of note, all patients received warfarin anti-coagulation in accord with contemporary practice (Humbert et al., "Treatment of Pulmonary Arterial Hypertension," *New Engl. J. Med.* 351(14):1425-36 (2004); Rich et al., "The Effect of High Doses of Calcium-Channel Blockers on Survival in Primary Pulmonary Hypertension," *New Engl. J. Med.* 327(2):76-81 (1992), each of which is hereby incorporated by reference in its entirety).

Discussion of Examples 1-3

This is the first report of an experimental PAH model with concentric luminal obliteration and plexiform lesions, two important histologic features of the human disease. Young rats subjected to MCT one week after pneumonectomy developed a degree of pulmonary hypertension and RV hypertrophy much greater than those treated with MCT following sham operation, as previously reported (Okada et al., "Pulmonary Hemodynamics Modify the Rat Pulmonary Artery Response to Injury. A Neointimal Model of Pulmonary Hypertension," *Am. J. Pathol.* 151(4):1019-25 (1997), which is hereby incorporated by reference in its entirety). The rats died earlier than those in earlier reports, and it is believed that the plexiform-like lesions are part of a more severe phenotype.

The administration of MCT one week following pneumonectomy has been used by other authors to model PAH in rats by other authors (Okada et al., "Pulmonary Hemodynamics Modify the Rat Pulmonary Artery Response to Injury. A Neointimal Model of Pulmonary Hypertension," *Am. J. Pathol.* 151(4): 1019-25 (1997); Nishimura et al., "Simvastatin Rescues Rats from Fatal Pulmonary Hypertension by Inducing Apoptosis of Neointimal Smooth Muscle Cells," *Circulation* 108(13):1640-5 (2003), each of which is hereby incorporated by reference in its entirety). However, these previous investigations involved the use of animals 350 to 400 g (about 12 weeks), and the rats did not exhibit plexiform lesions following MCT treatment. In contrast, the present study involved the selection of younger animals (200 g, 6 weeks), and the observation of vascular pathology strikingly similar to that found in the human PAH disease was both unexpected and dramatic. Rats have a remarkable ability for lung proliferation (following contralateral pneumonectomy) that has been recognized for over 25 years (Brody, "Time Course of and Stimuli to Compensatory Growth of the Lung after Pneumonectomy," *J. Clin. Invest.* 56(4):897-904 (1975), which is hereby incorporated by reference in its entirety). It may be that younger rats are more prone to have vascular cell proliferation in response to the combined stimulus of endothelial injury (MCT) and pneumonectomy. Given the results demonstrated above, the rat model described herein is believed to be an appropriate tool for studying the mechanisms that underlie the vascular cell proliferation characteristic of the human disorder (Tuder et al., "Exuberant Endothelial Cell Growth and Elements of Inflammation are Present in Plexiform Lesions of Pulmonary Hypertension," *Am. J. Pathol.* 144(2):275-85 (1994); Cool et al., "Three-Dimensional Reconstruction of Pulmonary Arteries in Plexiform Pulmonary Hypertension Using Cell-Specific Markers. Evidence for a Dynamic and Heterogeneous Process of Pulmonary Endothelial Cell Growth," *Am. J. Pathol.* 155(2):411-9 (1999); Tuder et al., "Expression of Angiogenesis-Related Molecules in Plexiform Lesions in Severe Pulmonary Hypertension: Evidence for a Process of Disordered Angiogenesis," *J. Pathol.* 195(3):367-74 (2001); Tuder et al., Monoclonal Endothelial Cells in Appetite Suppressant-Associated Pulmonary Hypertension," *Am. J. Respir. Crit. Care Med.* 158 (6):1999-2001 (1998), each of which is hereby incorporated by reference in its entirety).

Cool et al. used two endothelial antigens (vWF and VEGF-R2) to distinguish between immature endothelial cells (or those from a hematopoietic lineage) from those with a more mature endothelial phenotype (Cool et al., "Three-Dimensional Reconstruction of Pulmonary Arteries in Plexiform Pulmonary Hypertension Using Cell-Specific Markers. Evidence for a Dynamic and Heterogeneous Process of Pulmonary Endothelial Cell Growth," *Am. J. Pathol.* 155(2):411-9 (1999), which is hereby incorporated by reference in its entirety). In that report, immature endothelial cells staining with VEGF-R2 were found throughout human plexiform lesions while mature endothelial cells expressing vWF were only found lining the lumens of the vascular spaces. The data presented in FIG. 3 suggest that some of these lesions do have abundant endothelial cells, and the pattern of endothelial cell staining suggests that immature and mature endothelial cells are present, similar to the human disease. Human autopsy data, reported by Cool et al. (above), has suggested the possibility that the lesions are an active part of the pathology that precedes concentric luminal obliteration. In that report, plexiform lesions appeared at branch points, and the pattern of antigen expression suggested that the most actively proliferating cells were in areas of increased sheer stress. The three-dimensional reconstructions showed that actively dividing cells in plexiform lesions ultimately "burned out" to occlude the lumen with a concentric "onion skin" lesion immediately proximal to the branch point. Thus, the young rat model described herein should allow for confirmation that plexiform lesions are an important part of the pathology that leads to concentric luminal obliteration.

The above data also addresses another question about the plexiform lesions that has previously been difficult to answer in humans. The presence of heavy VEGF antigen staining and endothelial cells with VEGF message has prompted some investigators to suggest that plexiform lesions are a form of disorganized angiogenesis (Tuder et al., "Expression of Angiogenesis-Related Molecules in Plexiform Lesions in Severe Pulmonary Hypertension: Evidence for a Process of Disordered Angiogenesis," *J. Pathol.* 195(3):367-74 (2001), which is hereby incorporated by reference in its entirety). Implicit in this language is the assumption that these plexiform lesions are connected to the pulmonary arterial circulation. In humans, it has not been possible to test this assumption directly, although recent advances in the resolution of contrasted CT and MRI may facilitate direct visualization of lesions in living patients. Nevertheless, in the young rodent model, the vascular appearing structures contain microspheres that were delivered through the main pulmonary artery at the time of sacrifice (FIG. 3). This provides evidence that these structures are connected to the pulmonary circulation and that they represent a disorganized angiogenesis as previously hypothesized.

The finding of increased TF expression in patients and rats with PAH suggests an explanation for the in situ thrombosis first observed in autopsy studies over 20 years ago (Fuster et al., Primary Pulmonary Hypertension: Natural History and the Importance of Thrombosis," *Circulation* 70(4):580-7 (1984), which is hereby incorporated by reference in its entirety). In that first report of largely clinical data, not all patients had autopsies. However, by clinical criteria, the patients had primary pulmonary hypertension (now called idiopathic PAH), and yet in situ thrombosis was a major finding in the autopsies that were performed. A second autopsy series examined specimens from 58 patients in the initial NHLBI Primary Pulmonary Hypertension Registry (Pietra et al., "Histopathology of Primary Pulmonary Hypertension. A Qualitative and Quantitative Study of Pulmonary Blood Vessels from 58 Patients in the National Heart, Lung, and Blood Institute, Primary Pulmonary Hypertension Registry," *Circulation* 80(5):1198-206 (1989), which is hereby incorporated by reference in its entirety). In this carefully selected group of patients with idiopathic disease, nineteen patients had thrombotic lesions. Recanalized thrombi were observed in 9/25 patients with plexiform lesions (Pietra et al., "Histopathology of Primary Pulmonary Hypertension. A Qualitative and Quantitative Study of Pulmonary Blood Vessels from 58 Patients in the National Heart, Lung, and Blood Institute, Primary Pulmonary Hypertension Registry," *Circulation* 80(5):1198-206 (1989), which is hereby incorporated by reference in its entirety), demonstrating that in situ thrombosis and plexiform lesions co-exist in some patients with idiopathic disease.

Clinical data also supports the idea that PAH is a disease with a thrombotic diathesis, since two different observational data sets have suggested that warfarin anticoagulation may be beneficial (Kawut et al., "New Predictors of Outcome in Idiopathic Pulmonary Arterial Hypertension," *Am. J. Cardiol.* 95(2): 199-203 (2005); Rich et al., "The Effect of High Doses of Calcium-Channel Blockers on Survival in Primary Pulmonary Hypertension," *New Engl. J. Med.* 327(2):76-81 (1992), which is hereby incorporated by reference in its entirety). The first was an examination of mortality determinants in a prospective observational trial of high dose calcium channel blockade performed in the early 1990's, as reported by Rich et al. (referenced above). All patients given warfarin had lung scans that suggested "non-uniform" pulmonary blood flow but none met clinical criteria to diagnose pulmonary embolic disease. Warfarin use was associated with decreased mortality at 5 years. Prostanoid therapy reduces platelet aggregation and serum evidence for endothelial activation (Friedman et al., "Continuous Infusion of Prostacyclin Normalizes Plasma Markers of Endothelial Cell Injury and Platelet Aggregation in Primary Pulmonary Hypertension," *Circulation* 96(9):2782-4 (1997), which is hereby incorporated by reference in its entirety), and thus one might have expected less benefit to warfarin in the prostacyclin era. However, the most recent report by Kawut (referenced above) observed survival in consecutive patients from Columbia Presbyterian (1994-2002) and included patients who were treated with advanced therapies such as prostacyclin. Kawut et al. still observed a survival benefit when patients were also treated with warfarin.

TF is normally present at very low levels in the intima and media of the arterial wall. Increased TF expression at the arterial luminal surface would predispose to the in situ thrombosis commonly seen in PAH. The findings of increased TF expression in the arterial wall of rats and humans with severe PAH (see Examples 2-3 above) thus suggests an explanation for the thrombotic diathesis seen in PAH.

The increase in TF may play other roles in the pathogenesis of PAH. TF activation produces factor Xa and thrombin, both of which regulate intracellular signaling in vascular endothelial cells (EC) and smooth muscle cells (SMC) via protease activated receptor (PAR) family members (Riewald et al., Orchestration of Coagulation Protease Signaling by Tissue Factor," *Trends Cardiovasc. Med.* 12(4):149-54 (2002); Coughlin, "Protease-Activated Receptors in Vascular Biology," *Thromb. Haemost.* 86(1):298-307 (2001), each of which is hereby incorporated by reference in its entirety). Thrombin increases endothelial permeability and promotes SMC migration and proliferation (Patterson et al., "New Tricks for Old Dogs: Nonthrombotic Effects of Thrombin in Vessel Wall Biology," *Circ. Res.* 88(10): 987-97 (2001), which is hereby incorporated by reference in its entirety) through interaction with its G-protein coupled PAR receptor. PAR activation also mediates adhesion molecule expression and thus influences inflammatory cell recruitment (Rahman et al., "Protein Kinase C-Delta Regulates Thrombin-Induced ICAM-1 Gene Expression in Endothelial Cells via Activation of p38 Mitogen-Activated Protein Kinase," *Mol. Cell Biol* 21(16):5554-65 (2001); Rahman et al., "G-alpha(q) and G-betagamma Regulate PAR-1 Signaling of Thrombin-Induced NF-KappaB Activation and ICAM-1 Transcription in Endothelial Cells," Circ. Res. 91(5):398-405 (2002), which is hereby incorporated by reference in its entirety). In SMC and EC derived from the aorta, TF expression is sensitive to shear, strain, hypoxia, growth factors (VEGF), and the chemokine MCP-1 (Schecter et al., "Tissue Factor is Induced by Monocyte Chemoattractant Protein-1 in Human Aortic Smooth Muscle and THP-1 Cells," *J. Biol. Chem.* 272(45):28568-73 (1997); Yan et al., "Protein Kinase C-Beta and Oxygen Deprivation. A Novel Egr-1-Dependent Pathway for Fibrin Deposition in Hypoxemic Vasculature," *J. Biol. Chem.* 275(16): 11921-8 (2000); Lin et al., "Shear Stress Induction of the Tissue Factor Gene," *J. Clin. Invest.* 99(4):737-44 (1997); Silverman et al., "Tissue Factor Expression is Differentially Modulated by Cyclic Mechanical Strain in Various Human Endothelial Cells," *Blood Coagul. Fibrinolysis* 7(3):281-8 (1996), each of which is hereby incorporated by reference in its entirety). Since these factors are thought to be involved in the pathogenesis of PH, increased TF expression is likely a downstream mediator of a number of the signals already thought to promote vascular remodeling in PAH.

TF inhibitors markedly attenuate intimal hyperplasia following experimental injury to vessels of the systemic circulation: systemic infusion of recombinant tissue factor pathway inhibitor (TFPI) following carotid injury in rats reduced the neointimal formation measured at 28 days (Han et al., "Structural Requirements for TFPI-Mediated Inhibition of Neointimal Thickening After Balloon Injury in the Rat," *Arterioscler. Thromb. Vasc. Biol.* 19(10):2563-7 (1999), which is hereby incorporated by reference in its entirety). Local gene transfer of TFPI reduced neointimal formation in the carotid arteries of rabbits after balloon injury (Zoldhelyi et al., "Local Gene Transfer of Tissue Factor Pathway Inhibitor Regulates Intimal Hyperplasia in Atherosclerotic Arteries," *Proc. Nat. Acad. Sci. USA* 98(7):4078-83 (2001), which is hereby incorporated by reference in its entirety). Swine undergoing coronary angioplasty followed by prolonged TFPI infusion had markedly less neointimal formation at 28 days (Roque et al., "Inhibition of Tissue Factor Reduces Thrombus Formation and Intimal Hyperplasia After Porcine Coronary Angioplasty," *J. Amer. Coll. Cardiol.* 36(7):2303-10 (2000), which is hereby incorporated by reference in its entirety). Finally, TF deficient mice were created by rescuing the lethal phenotype of the homozygous knockout mouse with low level expression of human TF on a mini gene. Compared to wild type litter mates, TF deficient mice had a marked reduction in neointimal formation following wire injury of the femoral artery. Importantly, this model has very little thrombosis even in the wild type animals, and thus the loss of the procoagulant effect of TF is not a likely explanation for the change in neointima (Pyo et al., "Mice Deficient in Tissue Factor Demonstrate Attenuated Intimal Hyperplasia in Response to Vascular Injury and Decreased Smooth Muscle Cell Migration," *Thromb. Haemost.* 92(3):451-8 (2004), which is hereby incorporated by reference in its entirety). It has been hypothesized that the change in neointimal formation in the TF-deficient model was attributable to the downstream signaling effects of TF mediated by thrombin or Factor Xa.

Increased TF activity might mediate the disorganized angiogenesis and cellular proliferation seen in plexiform lesions, because TF activity has been linked to angiogenesis (Mackman, "Role of Tissue Factor in Hemostasis, Thrombosis, and Vascular Development," *Arterioscler. Thromb. Vasc. Biol.* 24(6):1015-22 (2004), which is hereby incorporated by reference in its entirety) and the cellular proliferation following injury to the systemic circulation (Pyo et al., "Mice Deficient in Tissue Factor Demonstrate Attenuated Intimal Hyperplasia in Response to Vascular Injury and Decreased Smooth Muscle Cell Migration," *Thromb. Haemost.* 92(3): 451-8 (2004), which is hereby incorporated by reference in its entirety).

In summary, the above examples demonstrate a rat model of PAH with severe hemodynamic alterations, neointimal formation, and plexiform-like lesions. The lesions have a pattern of endothelial antigen staining similar to human plexiform lesions, and they are connected to the main pulmonary artery. Intense TF staining was found in the plexiform-like lesions and vessels of these rats. The rat model will allow investigation of the signaling which generates plexiform lesions and their causal relationship in severe PAH. Finally, the model offers a means to test novel therapeutic strategies for their ability to prevent lesions or even cause regression of established plexiform lesions.

Example 4

Administration of Tissue Factor Pathway Inhibitor to Treat PAH in Rat Model

Ixolaris (IXO) is a TFPI mimetic that was isolated from the saliva of a hemophagic ixodid tick, *Ixodes scapularis* (Lai et al., "A Thrombin Inhibitor from the Ixodid Tick, *Amblyomma hebraeum*," *Gene* 342(2):243-249 (2004), which is hereby incorporated by reference in its entirety). This protein has been cloned and recombinantly produced in high quantity in a baculovirus system by Dr. Ivo Francischetti at the National Institutes of Allergy and Infectious Disease, and he provided the reagent for the work described herein. As a TFPI mimetic, IXO acts at a proximal site (i.e., generation of Factor Xa) to block TF activity.

Figure 5:
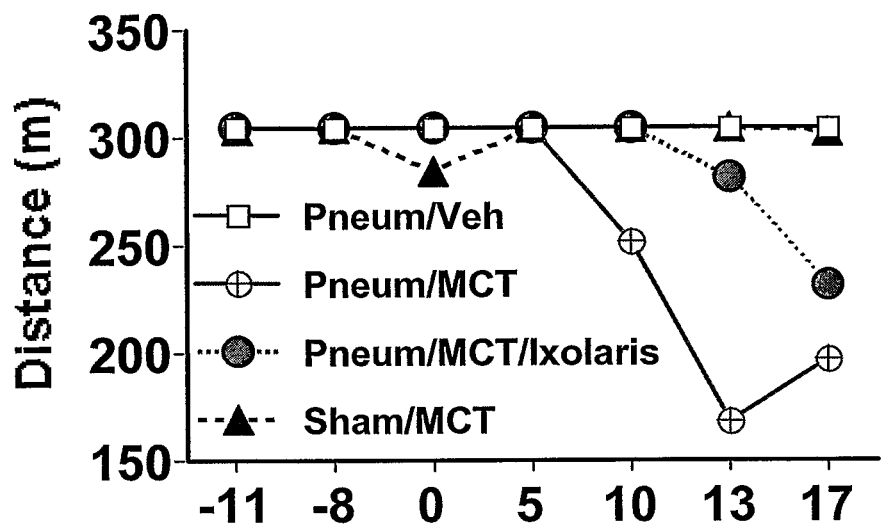
FIG. 5 is a graph that illustrates the results of treadmill tests on rats from four rat groups: Pneum/Veh; Pneum/MCT; sham/MCT; and Pneum/MCT/IXO.
Figure 6:
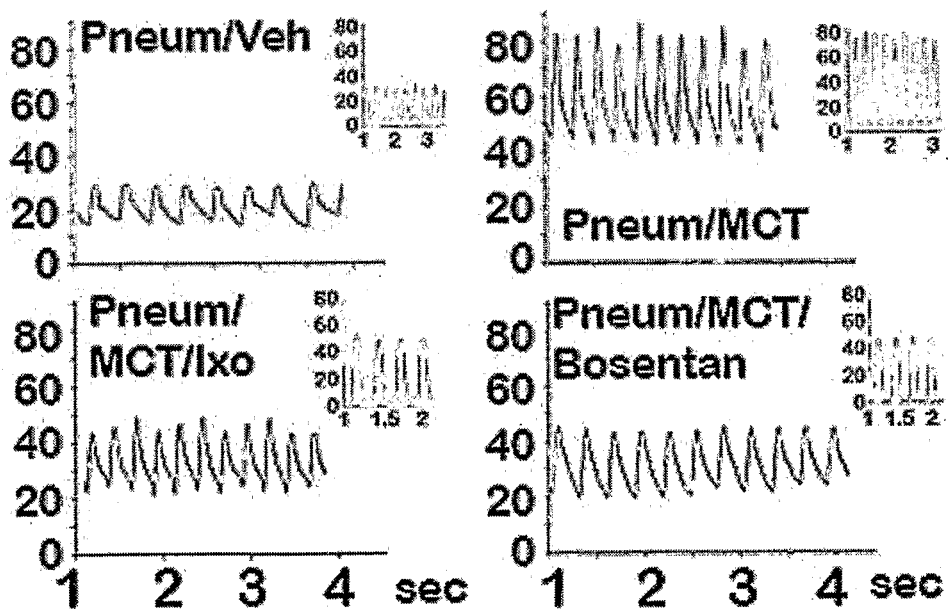
FIG. 6 is a series of graphs that illustrate pulmonary arterial ("PA") and right ventricular ("RV") pressure tracings from rats treated as indicated and sacrificed at 21 days.
Figure 7:
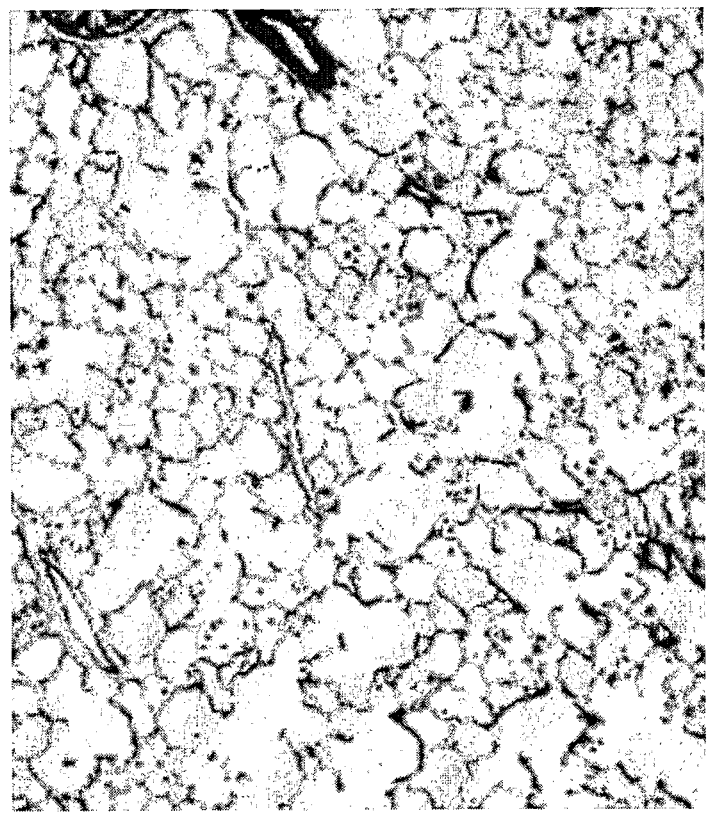
FIG. 7 is an image of elastin-trichrome stain for a lung tissue sample obtained from Pneum/MCT/IXO rat sacrificed at day 21 (4× magnification).

Three Pneum/MCT rats were treated with IXO (40 µg/kg S.Q. daily) beginning 5 days after MCT and continuing for 8 days. Compared with controls, the rats exhibited a substantial improvement in exercise capacity (FIG. 5), and none of them fell below the seven min. threshold, a performance that predicts premature death. One IXO treated rat sacrificed at 21 days had only a modest elevation in PA pressure (FIG. 6), similar to what was found with bosentan (100 mg/kg daily), the mainstay of current oral PAH therapy. The histology was remarkably improved (FIG. 7): plexiform lesions were absent, luminal narrowing was attenuated, and obliterated vessels were rare. This is unlike any Pneum/MCT rat that was similarly analyzed. The other two IXO treated rats could not be evaluated, because they died at day 20, which was quite surprising given their exercise performance and the fact that spontaneous deaths are rarely observed in rats able to run longer than seven min at day 17. This suggests that their deaths may have been due to IXO toxicity, such as intracranial hemorrhage. Alternatively, disease recrudescence and death may have occurred because IXO treatment stopped at day 13.

This experiment will be repeated with longer IXO administration and varied dosage for purposes of assessing the efficacy versus toxicity of IXO.

Example 5

Administration of Monoclonal Antibody to Treat PAH in Rat Model

A set of species-specific monoclonal antibodies provided by Dr. Daniel Kirchhofer (Genentech), including those that bind and block TF activity and those that bind but do not block TF activity (as controls), will be tested in the rat PAH model described above. In surface plasmon resonance binding experiments, the 6H4 monoclonal antibody was demonstrated to bind with a $K_D$ of ~1 nM, whereas the 5A4 monoclonal antibody has a $K_D$ value of ~100 pM. In vitro experiments to measure the enzymatic activity of the VIIa/TF complex have demonstrated that 6H4 has an $IC_{50}$ at a dose of 5 µg/ml while 5A4 was less potent with an $IC_{50}$ at 40 µg/ml. In addition, both antibodies (at 10 mg/kg) had similar and marked effects on blood loss after tail bleeding (combined primary and secondary blood loss increased from 90 µl to 600 µl).

The monoclonal antibodies will be administered individually to rat PAH models beginning on day 5 post-MCT and concluding on one of several days (i.e., 9, 13, 17, 21, etc.). The PA pressure will be monitored in all rats, and on day 28 post-pneumo the rats will be sacrificed. Lung tissue samples will be examined for histological evidence of PAH. It is expected that one or both of the 6H4 and 5A4 monoclonal antibodies will inhibit TF and improve PAH symptoms and histological perturbations.

Example 6

Ex Vivo Transformation of Endothelial Progenitor Cells Expressing TFPI as Administration of Transformed Cells to PAH Rat Model Using the procedures reported in Zhao et al. ("Rescue of Monocrotaline-Induced Pulmonary Arterial Hypertension Using Bone Marrow-Derived Endothelial-Like Progenitor Cells: Efficacy of Combined Cell and eNOS Gene Therapy in Established Disease," *Circ. Res.* 96(4):442-450 (2005), which is hereby incorporated by reference in its entirety), endothelial progenitor cells will be isolated and transfected. The ex vivo transfected cells will be administered to rat PAH models either via peripheral intravenous route or via right ventricular catheterization. Introduction of the cells will begin on day 5 post-MCT and conclude on one of several days (i.e., 9, 13, 17, 21, etc. post-MCT). Exercise capacity will be measured as described above. The PA pressure will be monitored in all rats, and on day 28 post-pneumo the rats will be sacrificed. Lung tissue samples will be examined for histological evidence of PAH. It is expected that the ex vivo transformation will inhibit TF and improve PAH symptoms and histological perturbations.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of inhibiting development of a neointimal or plexiform lesion in lung vascular tissue of a patient having pulmonary arterial hypertension, the method comprising:
   providing a therapeutic agent selected from the group consisting of a tissue factor pathway inhibitor (TFPI) and a protease activated receptor 1 (PAR1) antagonist; and
   administering the therapeutic agent to the patient to contact vascular cells in lung vascular tissue with the therapeutic agent, wherein said contacting inhibits development of a neointimal or plexiform lesion in lung vascular tissue of the patient.

2. The method according to claim 1 wherein the therapeutic agent is selected from the group of recombinant TFPI, Ixolaris, SCH205831, FR171113, RWJ58259, SCH203099, SCH79797, and 3-mercaptoproprionyl-Phe-Cha-Cha-Arg-Lys-Pro-Asn-Asp-Lys-NH2 (SEQ ID NO: 1).

3. The method according to claim 1 wherein the vascular cells are endothelial cells, vascular smooth muscle cells, inflammatory cells, or a combination thereof.

4. The method according to claim 1 wherein the patient is a mammal.

5. The method according to claim 4 wherein the mammal is a rodent, dog, cat, cow, horse, sheep, pig, llama, alpaca, non-human primate, or human.

6. A method of treating pulmonary arterial hypertension comprising:
   providing a therapeutic agent selected from the group consisting of a tissue factor pathway inhibitor (TFPI) and a protease activated receptor 1 (PAR1) antagonist; and
   administering the therapeutic agent to a patient symptomatic with pulmonary arterial hypertension, wherein said administering is effective to reduce the extent of plexiform lesions or to reduce the extent of neointimal obliteration of small vessels in lung vascular tissue, thereby enhancing vascular capacity and treating pulmonary arterial hypertension.

7. The method according to claim 6 wherein the therapeutic agent is selected from the group of recombinant TFPI, Ixolaris SCH205831, FR171113, RWJ58259, SCH203099, SCH79797, and 3-mercaptoproprionyl-Phe-Cha-Cha-Arg-Lys-Pro-Asn-Asp-Lys-NH2 (SEQ ID NO: 1).

8. The method according to claim 6 wherein the plexiform lesions or the neointimal obliteration comprise endothelial cells, vascular smooth muscle cells, inflammatory cells, or a combination thereof.

9. The method according to claim 6 wherein the patient is a mammal.

10. The method according to claim 9 wherein the mammal is a rodent, dog, cat, cow, horse, sheep, pig, llama, alpaca, non-human primate, or human.

11. The method according to claim 6 wherein said administering is carried out orally, by inhalation, by intranasal instillation, topically, transdermally, parenterally, subcutaneously, intravenous injection, intra-arterial injection, intramuscular injection, intrapleural instillation, intraperitoneally injection, intraventricularly, intralesionally, or by application to mucous membranes.

12. A method of inhibiting the loss of small blood vessel beds associated with an arterial trunk in lung tissue of a patient having pulmonary arterial hypertension, the method comprising:
   providing a therapeutic agent selected from the group consisting of a tissue factor pathway inhibitor (TFPI) and a protease activated receptor 1 (PAR1) antagonist; and
   administering the therapeutic agent to the patient to contact vascular cells in a small blood vessel bed associated with an arterial trunk in lung tissue with the therapeutic agent, wherein said contacting inhibits vascular cell loss in the small blood vessel bed.

13. The method according to claim 12 wherein the therapeutic agent is selected from the group of recombinant TFPI, Ixolaris, SCH205831, FR171113, RWJ58259, SCH203099, SCH79797, and 3-mercaptoproprionyl-Phe-Cha-Cha-Arg-Lys-Pro-Asn-Asp-Lys-NH$_2$(SEQ ID NO: 1).

14. The method according to claim 12 wherein the vascular cells are endothelial cells, vascular smooth muscle cells, inflammatory cells, or a combination thereof.

15. The method according to claim 12 wherein the patient is a mammal.

16. The method according to claim 15 wherein the mammal is a rodent, dog, cat, cow, horse, sheep, pig, llama, alpaca, non-human primate, or human.

17. The method according to claim 1, wherein the therapeutic agent is a PAR1 antagonist.

18. The method according to claim 6, wherein the therapeutic agent is a PAR1 antagonist.

19. The method according to claim 12, wherein the therapeutic agent is a PAR1 antagonist.

* * * * *